US012778642B2

(12) United States Patent
Wolfe et al.

(10) Patent No.: US 12,778,642 B2
(45) Date of Patent: Nov. 3, 2026

(54) ANTERIOR CERVICAL PLATE ASSEMBLY

(71) Applicant: GLOBUS MEDICAL, INC., Audubon, PA (US)

(72) Inventors: Daniel Wolfe, Quakertown, PA (US); Jason Zappacosta, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 18/761,424

(22) Filed: Jul. 2, 2024

(65) Prior Publication Data

US 2024/0350179 A1 Oct. 24, 2024

Related U.S. Application Data

(63) Continuation of application No. 17/702,841, filed on Mar. 24, 2022, now Pat. No. 12,023,071, which is a continuation of application No. 16/407,284, filed on May 9, 2019, now Pat. No. 11,304,734, which is a continuation-in-part of application No. 16/356,760, filed on Mar. 18, 2019, now Pat. No. 11,272,963, which is a continuation-in-part of application No. 15/814,490, filed on Nov. 16, 2017, now Pat. No. 11,229,460.

(51) Int. Cl.

| | |
|---|---|
| ***A61B 17/80*** | (2006.01) |
| ***A61B 17/70*** | (2006.01) |
| ***A61B 17/86*** | (2006.01) |
| *A61B 17/00* | (2006.01) |

(52) U.S. Cl.

CPC ...... *A61B 17/7059* (2013.01); *A61B 17/8014* (2013.01); *A61B 17/8042* (2013.01); *A61B 17/8615* (2013.01); *A61B 2017/00862* (2013.01)

(58) Field of Classification Search

CPC ............ A61B 17/8014; A61B 17/8042; A61B 17/8605; A61B 17/8615

See application file for complete search history.

(56) References Cited

U.S. PATENT DOCUMENTS

| | | | | |
|---|---|---|---|---|
| 3,915,162 A | 10/1975 | Miller | | |
| 6,503,250 B2 | 1/2003 | Paul | | |
| 6,527,776 B1 | 3/2003 | Michelson | | |
| 6,602,255 B1 | 8/2003 | Campbell et al. | | |
| 6,793,658 B2 * | 9/2004 | LeHuec | ............... | A61B 17/808 606/280 |

(Continued)

FOREIGN PATENT DOCUMENTS

| | | |
|---|---|---|
| JP | 2008539822 | 11/2008 |
| WO | 2008019119 A2 | 2/2008 |

*Primary Examiner* — Anu Ramana

(57) ABSTRACT

A cervical plate assembly is disclosed. The cervical plate assembly includes a base plate including: (1) at least two bone screw seats, each bone screw seat including a borehole dimensioned to receive a bone screw, and (2) a first blocking seat positioned between the at least two bone screw seats. The cervical plate assembly includes a blocking mechanism retained within the first blocking seat of the base plate. The blocking mechanism is selectively positionable between a closed position in which the blocking mechanism obstructs at least one bone screw seat to retain a bone screw with the base plate, and an open position in which the bone screw seats are unobstructed.

10 Claims, 33 Drawing Sheets

(56) References Cited

U.S. PATENT DOCUMENTS 7,182,782 B2 2/2007 Kirschman
7,641,701 B2 1/2010 Kirschman
7,662,154 B2 2/2010 Ribiero
7,727,265 B2 6/2010 Paul
7,727,266 B2 6/2010 Lindemann et al.
7,887,547 B2 2/2011 Campbell et al.
8,043,346 B2 10/2011 Markworth
8,061,517 B2 11/2011 Loeffler et al.
8,066,750 B2 * 11/2011 Oi ...................... A61B 17/8042 606/289
8,079,518 B2 12/2011 Turner et al.
8,136,728 B2 3/2012 Turner et al.
8,196,825 B2 6/2012 Turner et al.
8,216,285 B2 7/2012 Markworth
8,287,550 B2 10/2012 Campbell et al.
8,343,194 B2 1/2013 Aflatoon
8,372,152 B2 2/2013 Kirschman
8,454,666 B2 6/2013 Tornier
8,454,667 B2 * 6/2013 Humphreys ....... A61B 17/8042 606/295
8,556,074 B2 10/2013 Turner et al.
8,662,299 B2 3/2014 Pratt et al.
8,668,723 B2 3/2014 Altarac et al.
8,734,496 B2 5/2014 Campbell et al.
8,784,459 B2 7/2014 Kaufman et al.
8,821,553 B2 9/2014 Kirschman
8,940,030 B1 1/2015 Stein et al.
9,039,744 B2 5/2015 Goodman et al.
9,055,983 B1 6/2015 Radcliffe et al.
9,072,560 B2 7/2015 Doherty
9,078,718 B2 7/2015 Campbell
9,101,407 B2 8/2015 Altarac et al.
9,113,964 B2 8/2015 Altarac et al.
9,119,681 B2 9/2015 Kaufmann et al.
9,186,189 B2 11/2015 Campbell et al.
9,265,531 B2 2/2016 Ziolo
9,271,770 B2 3/2016 Costabile
9,351,775 B2 * 5/2016 Bush, Jr. ............ A61B 17/8615
9,381,093 B1 * 7/2016 Morris ............... A61B 17/8042
9,451,995 B1 9/2016 Olson
9,504,584 B1 11/2016 Stein et al.
9,532,819 B2 1/2017 Campbell
9,877,756 B2 1/2018 Costabile
9,911,019 B2 3/2018 Schoutens
9,913,672 B2 3/2018 Kaufmann et al.
9,913,730 B1 3/2018 Stein et al.
9,918,749 B2 3/2018 Altarac et al.
9,943,349 B2 4/2018 Ziolo
9,987,059 B2 6/2018 Baynham
10,105,169 B2 10/2018 Leak et al.
10,245,084 B2 4/2019 Kaufmann et al.
2002/0013586 A1 1/2002 Justis et al.
2005/0021032 A1 1/2005 Koo
2005/0059972 A1 3/2005 Biscup
2005/0192577 A1 9/2005 Mosca et al.
2005/0216027 A1 9/2005 Suh et al.
2006/0247639 A1 11/2006 Anderson
2007/0123884 A1 5/2007 Abdou
2007/0270880 A1 11/2007 Lindemann et al.
2008/0287999 A1 11/2008 Markworth
2010/0016901 A1 1/2010 Robinson
2010/0137916 A1 6/2010 Hynes et al.
2012/0010618 A1 1/2012 Markworth
2013/0023936 A1 1/2013 Altarac et al.
2013/0204300 A1 * 8/2013 Michelson ........... A61B 17/863 606/246
2014/0039554 A1 2/2014 Kim et al.
2015/0201982 A1 7/2015 Altarac et al.
2016/0128746 A1 5/2016 Dunaway
2016/0228156 A1 8/2016 Morris et al.
2017/0181781 A1 6/2017 Dubois et al.
2017/0196606 A1 7/2017 Cianfrani et al.
2017/0215930 A1 8/2017 Lauf et al.
2018/0185071 A1 7/2018 Altarac et al.
2019/0015139 A1 1/2019 Leak et al.
2019/0053838 A1 2/2019 Cook et al.

* cited by examiner

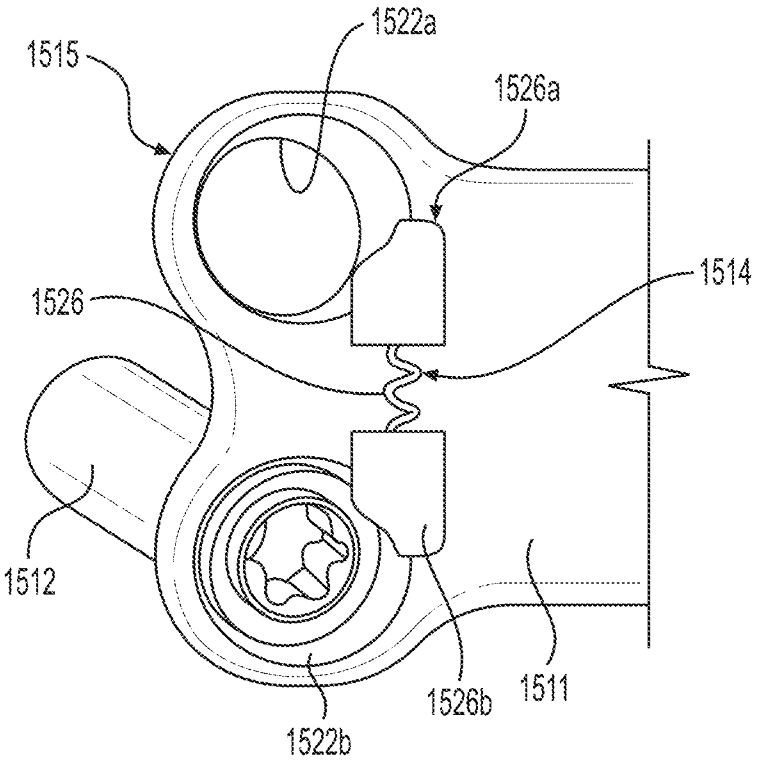
FIG. 18A
FIG. 18B
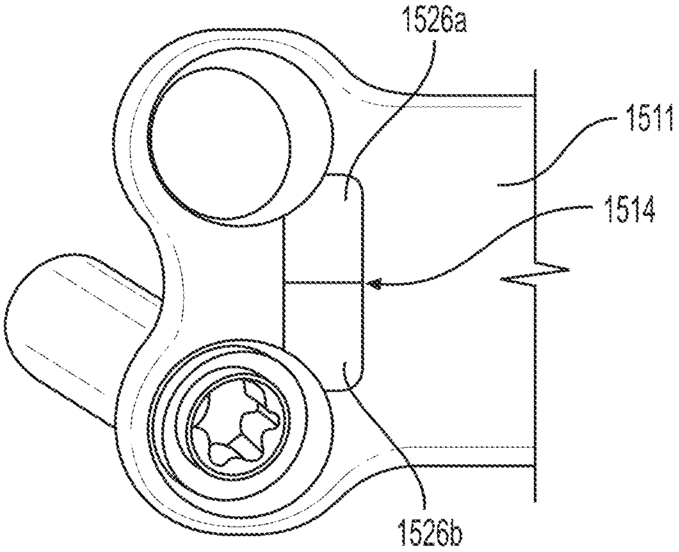

ANTERIOR CERVICAL PLATE ASSEMBLY

REFERENCE TO RELATED APPLICATIONS

The present application is a continuation of U.S. patent application Ser. No. 17/702,841, filed on Mar. 24, 2022, now U.S. Pat. No. 12,023,071 which is a continuation of U.S. patent application Ser. No. 16/407,284, filed on May 9, 2019, now U.S. Pat. No. 11,304,734 which is a continuation-in-part of U.S. Ser. No. 16/356,760, filed Mar. 18, 2019, now U.S. Pat. No. 11,272,963 which is a continuation-in-part of U.S. Ser. No. 15/814,490, filed Nov. 16, 2017, now U.S. Pat. No. 11,229,460 which is hereby incorporated by reference in its entirety for all purposes.

FIELD OF INVENTION

The present disclosure is related to a surgical implant, and is more particularly related to an anterior cervical plate.

BACKGROUND

Certain surgical procedures require a surgeon to fuse portions of a patient's spine to each other. Implanting a cervical plate reduces a patient's range of motion, and helps relieve pain experienced by a patient. Although cervical plate implantations are used to treat radiculopathy or myelopathy, but one of ordinary skill in the art would recognize that fusion can be used for other types of surgery.

Anterior cervical plate assemblies typically include a base plate defining through openings for bone screws to anchor the base plate to a patient's spine. Some cervical plate assemblies include a blocking mechanism to prevent the bone screws from inadvertently backing out of the base plate. One type of known blocking mechanism includes an automated blocking feature, such that once a bone screw passes a predetermined threshold then the blocking mechanism is automatically activated to block the bone screws from inadvertently backing out of the plate. These automated blocking mechanisms can be complicated for surgeons to operate, and can make removal of the base plate difficult.

Other known blocking mechanisms for anterior cervical plate assemblies rely on a patient's bones to have a certain strength characteristic to withstand the blocking mechanism features. Some known types of blocking mechanisms require force for removing a screw from the blocking mechanism. However, this type of blocking mechanism can cause stripping of the screw holes for bone screws implanted in a patient's bones.

Another known type of blocking mechanism for anterior cervical plate assemblies requires additional steps to install and lock the blocking mechanism screw in the plate. In some devices, this additional step requires a specialty tool or instrument. These steps are time consuming and require the surgeon to perform additional steps during surgery, which is undesirable.

It would be desirable to provide an improved cervical plate assembly that is relatively simple to use and provides a reliable blocking function.

SUMMARY

Briefly stated, an improved cervical plate assembly is disclosed. The cervical plate assembly includes a base plate including four bone screw seats. Each bone screw seat includes a borehole dimensioned to receive a bone screw.

Each borehole defines a central axis that is (a) angled relative to a central lateral axis of the base plate at a first angle and (b) angled relative to a central longitudinal axis at a second angle. In one embodiment, the first angle is at least 25 degrees, and the second angle is at least 6 degrees. The base plate defines two retention slots that are each positioned between a pair of the four bone screw seats. The assembly includes two blocking mechanisms. Each blocking mechanism includes a biasing element arranged between a first blocking element and a second blocking element. The first blocking element is configured to obstruct a first bone screw seat of the four bone screw seats, and the second blocking element is configured to obstruct a second bone screw seat of the four bone screw seats. The first blocking element and the second blocking element are independently positionable from each other. Each blocking mechanism is retained within a respective one of the two retention slots. The blocking mechanisms are selectively positionable between a closed position in which the blocking mechanism obstructs at least one bone screw seat to retain a bone screw with the base plate, and an open position in which the bone screw seats are unobstructed.

A variety of arrangements and embodiments are described in more detail below and in the claims.

BRIEF DESCRIPTION OF THE DRAWINGS

The foregoing summary as well as the following detailed description will be best understood when read in conjunction with the appended drawings. In the drawings:

FIG. 18A is a top view of a cervical plate assembly in a blocked position according to one embodiment.

FIG. 18B is a top view of the cervical plate assembly of FIG. 18A in an open position.

DETAILED DESCRIPTION OF THE PREFERRED EMBODIMENTS

Figure 1:
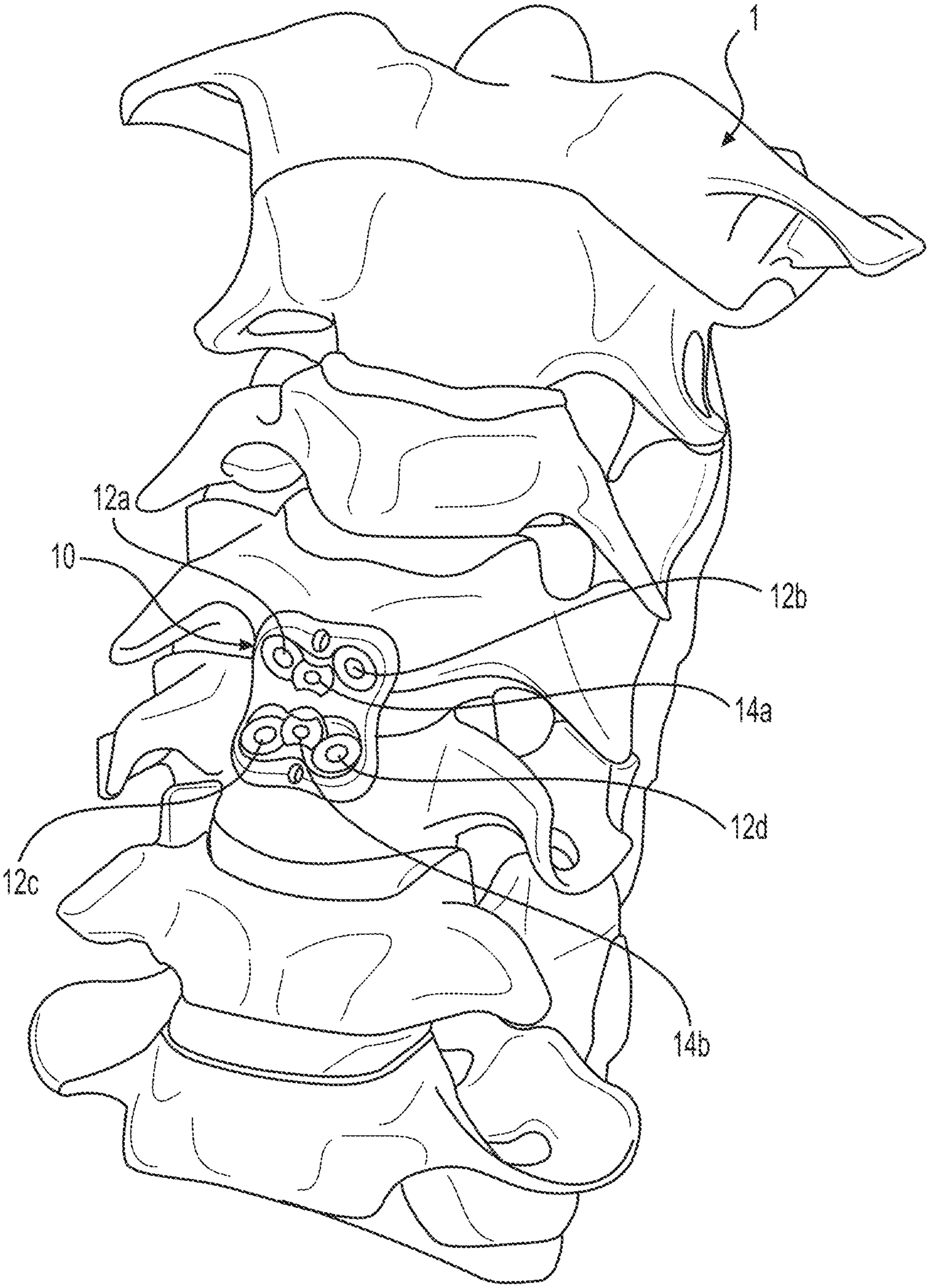
FIG. 1 is a perspective view of one embodiment of a cervical plate assembly implanted on a patient's spine.

It is to be understood that the present disclosure is not limited in its application to the details of construction and the arrangement of components set forth in the description herein or illustrated in the drawings. The teachings of the present disclosure may be used and practiced in other embodiments and practiced or carried out in various ways. Also, it is to be understood that the phraseology and terminology used herein is for the purpose of description and should not be regarded as limiting. The use of “including,” “comprising,” or “having” and variations thereof herein is meant to encompass the items listed thereafter and equivalents thereof as well as additional items. Unless specified or limited otherwise, the terms “mounted,” “connected,” “supported,” and “coupled” and variations thereof are used broadly and encompass both direct and indirect mountings, connections, supports, and couplings. Further, “connected” and “coupled” are not restricted to physical or mechanical connections or couplings.

The following discussion is presented to enable a person skilled in the art to make and use embodiments of the present disclosure. Various modifications to the illustrated embodiments will be readily apparent to those skilled in the art, and the principles herein can be applied to other embodiments and applications without departing from embodiments of the present disclosure. Thus, the embodiments are not intended to be limited to embodiments shown, but are to be given the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of the embodiments. Skilled artisans will recognize the examples provided herein have many useful alternatives and fall within the scope of the embodiments.

Figure 2:
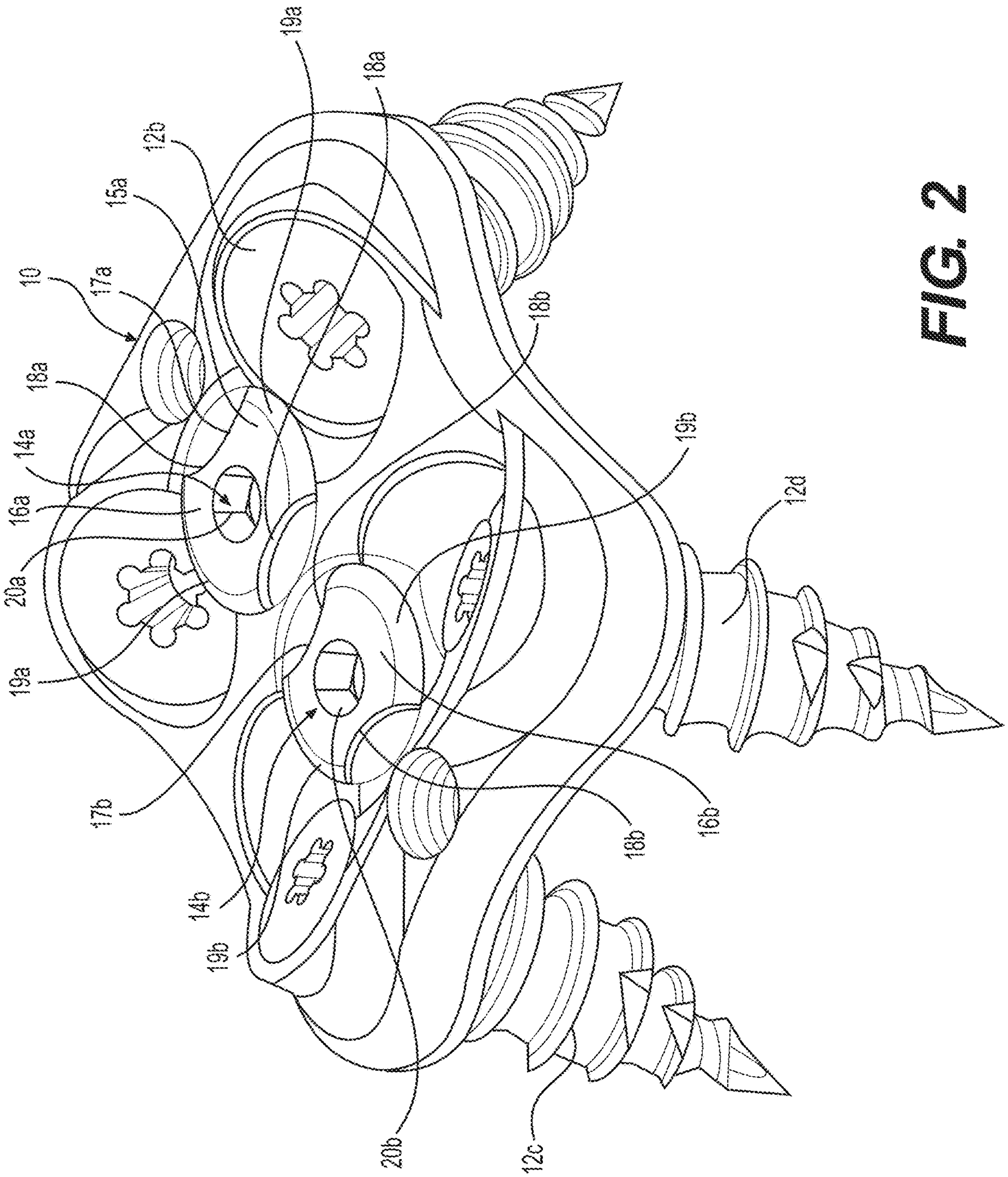
FIG. 2 is a perspective view of the cervical plate assembly of FIG. 1 including bone screws.

FIG. 1 illustrates a cervical region of a patient's spine 1 with an anterior cervical plate assembly 10 implanted on the spine 1. As shown in FIG. 1, the plate assembly 10 is implanted at the C4-C5 vertebrae of the spine 1. One of ordinary skill in the art would recognize that the plate assembly 10 could be installed at different regions of the patient's spine 1. The term plate assembly is generically used herein to generally refer to the plate assemblies described in some of the embodiments. In one embodiment, the plate assemblies are specifically designed to be used for anterior cervical implantations. One of ordinary skill in the art would understand from the present disclosure that the concepts and features of the plate assemblies disclosed herein could be adapted for surgical assemblies and techniques for other portions of a user's anatomy besides the spine. With respect to FIG. 1, the anterior cervical plate assembly 10 is shown including four bone screws 12*a*-12*d* and two blocking assemblies 14*a*, 14*b*, however one of ordinary skill in the art would recognize from the present disclosure that alternative arrangements of the anterior cervical plate assembly 10 could be used. For instance, the cervical plate assembly can extend to multiple levels of the spine and include additional screw holes for additional fixation to adjacent vertebral bodies. The bone screws used in any of the embodiments described herein can be self-drilling, self-tapping, variable angle, fixed angle, or any other known type of bone screw design. Additionally, the embodiments of the base plate described herein can be configured to accept bone screws having screw diameters of 4.2 mm and 4.6 mm, although one of ordinary skill in the art would understand that different sizes for bone screws can be used. FIG. 2 illustrates the plate assembly 10 with the bone screws 12*a*-12*d* and the blocking mechanisms 14*a*, 14*b* in an uninstalled state. As shown in FIG. 2, the plate assembly 10 includes two pairs of bone screws 12*a*-12*d*, with each pair configured to be implanted into a vertebral body. In this embodiment, the blocking mechanisms 14*a*, 14*b* each include a blocking screw 15*a*, 15*b*. The blocking screws 15*a*, 15*b* each include a head 16*a*, 16*b* with a varying circumferential edge 17*a*, 17*b*, and an engagement recess 20*a*, 20*b* configured to be engaged by a tool for rotationally driving the heads 16*a*, 16*b*. One of ordinary skill in the art would understand from the present disclosure that the geometry of the engagement recesses 20*a*, 20*b* can be varied. In one embodiment, the engagement recess can be omitted and the blocking mechanisms 14*a*, 14*b* can be manually engaged/actuated by a user.

As shown in FIG. 2, the circumferential edges 17*a*, 17*b* of the blocking screws 15*a*, 15*b* include diametrically opposed cutouts 18*a*, 18*b*, and diametrically opposed lobes 19*a*, 19*b*. The cutouts 18*a*, 18*b* are dimensioned to allow passage of the bone screws 12*a*-12*d* when the cutouts 18*a*, 18*b* overlap an associated bone screw seat. The lobes 19*a*, 19*b* are configured to obstruct an associated bone screw seat to block the bone screws 12*a*-12*d* from backing out of the plate assembly 10. The engagement recesses 20*a*, 20*b* are illustrated with a hexagonal profile, but one of ordinary skill in the art would recognize from the present disclosure that any non-round profile can be used. The heads 16*a*, 16*b* are engaged by a user and rotated a quarter turn, i.e. 90 degrees, to move from a blocked position, in which bone screws 12*a*-12*d* are retained with the plate assembly, to an open position, in which the bone screws 12*a*-12*d* can be removed from the plate assembly 10. As used herein, the blocked position corresponds to a position in which the bone screws seats are obstructed and the open position corresponds to a position in which the bone screw seats are unobstructed.

Figure 3B:
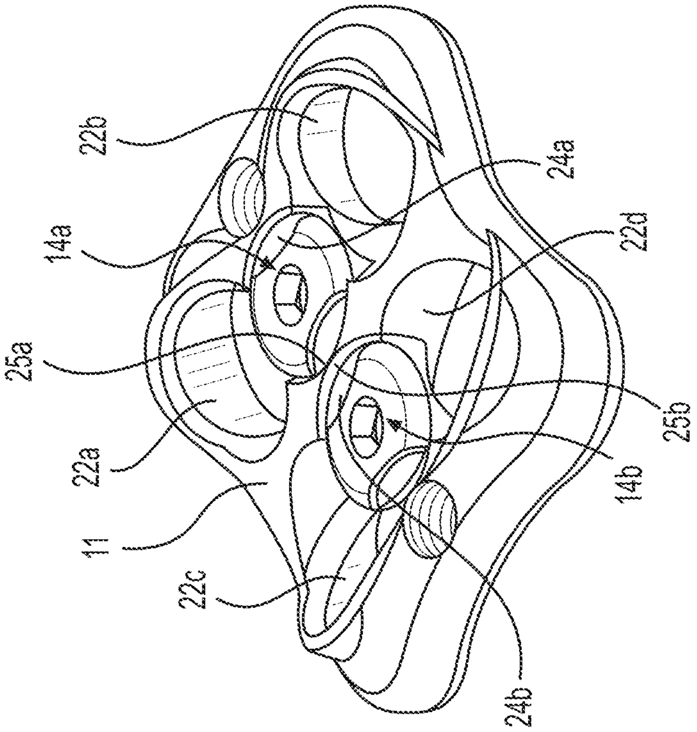
FIG. 3B is a perspective view of the cervical plate assembly of FIGS. 1-3A with the blocking mechanism in a blocked position.
Figure 3A:
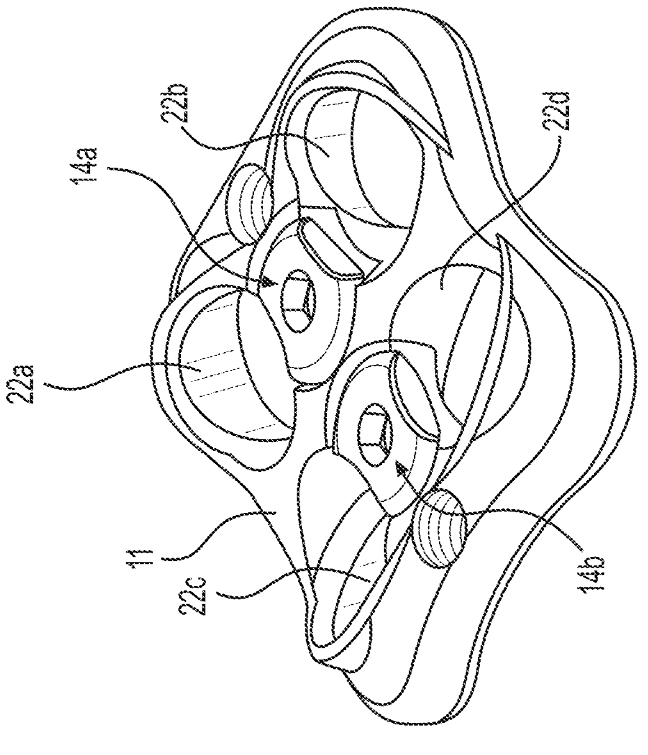
FIG. 3A is a perspective view of the cervical plate assembly of FIGS. 1 and 2 with a blocking mechanism in an open position.

FIG. 3A illustrates an open configuration for the blocking mechanisms 14*a*, 14*b*, and FIG. 3B illustrates a blocked configuration for the blocking mechanisms 14*a*, 14*b*. As shown in FIGS. 3A and 3B, the plate assembly 10 includes a base plate 11 that defines bone screw seats 22*a*-22*d* for a respective one of the bone screws 12*a*-12*d*. The plate 11 also defines blocking mechanism seats 24*a*, 24*b*, shown in FIG. 3B, which are configured to retain a respective one of the blocking mechanisms 14*a*, 14*b*. As illustrated in this embodiment, the blocking mechanism seats 24*a*, 24*b* include a retention lip 25*a*, 25*b* that prevents the blocking mechanisms 14*a*, 14*b* from being removed from the plate 11. One of ordinary skill in the art would recognize from the present disclosure that alternative retention arrangements could be provided for ensuring the blocking mechanisms 14*a*, 14*b* are retained with the plate 11. For example, the blocking mechanisms 14*a*, 14*b* could be retained with the plate 11 by tabs, prongs, clastic elements, slots, channels, or other retention features. In one embodiment, the blocking mechanisms 14*a*, 14*b* can include an enlarged head on an opposite end from the screw heads 16*a*, 16*b* and the plate 11 can define a retention recess dimensioned to captively secure the enlarged head of the blocking mechanisms 14*a*, 14*b*. One of ordinary skill in the art would recognize from the present disclosure that a variety of retention features could be used, as long as the retention features retain the blocking mechanisms 14*a*, 14*b* with the base plate 11 while also allowing the blocking mechanisms 14*a*, 14*b* to rotate.

Figure 4B:
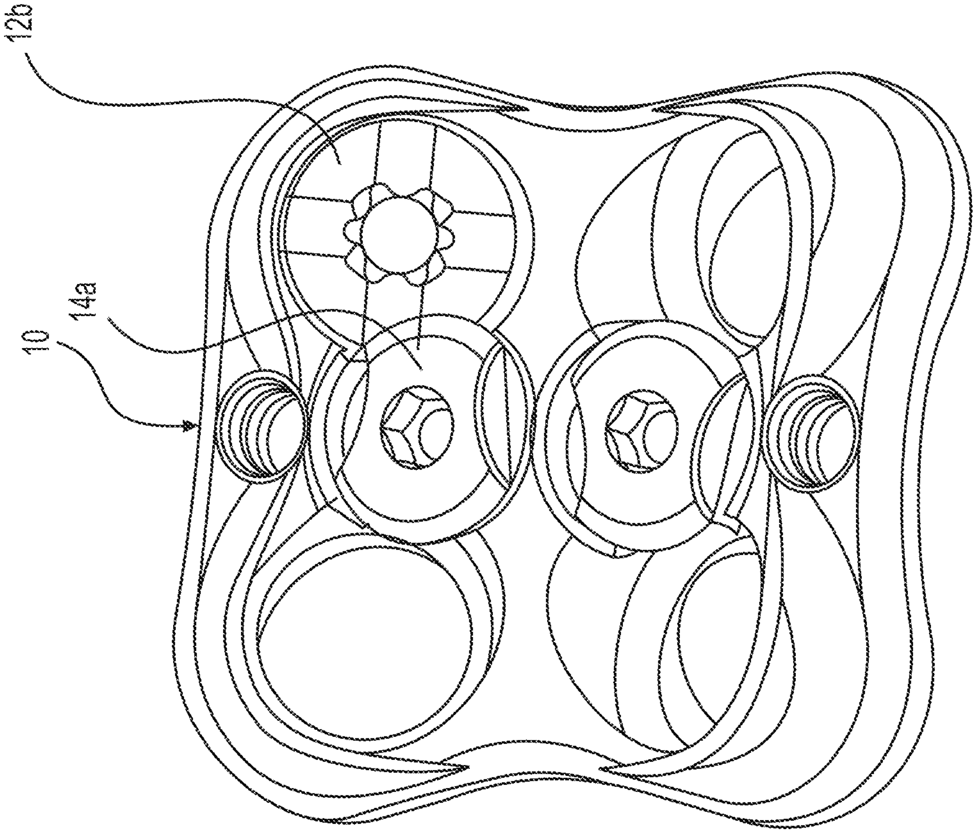
FIG. 4B is a top perspective view of the cervical plate assembly of FIGS. 1-4A including an installed bone screw with the blocking mechanism in the blocked position.
Figure 4A:
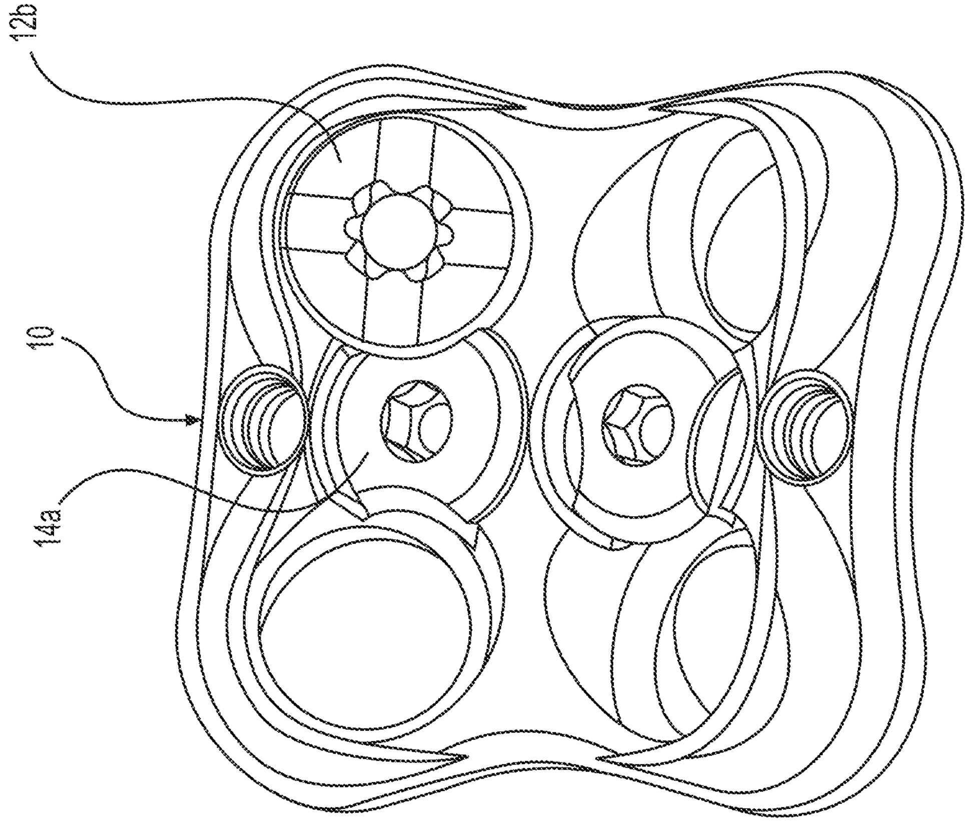
FIG. 4A is a top perspective view of the cervical plate assembly of FIGS. 1-3B including an installed bone screw with the blocking mechanism in the open position.

FIGS. 4A and 4B illustrate the plate assembly 10 including a single bone screw 12*b*. FIG. 4A illustrates the blocking mechanism 14*a* in an open position in which the bone screw 12*b* can be removed from the base plate 11. FIG. 4B illustrates the blocking mechanism 14*b* in a blocking position in which the bone screw 12*b* is blocked from backing out of the plate assembly 10.

Figure 5B:
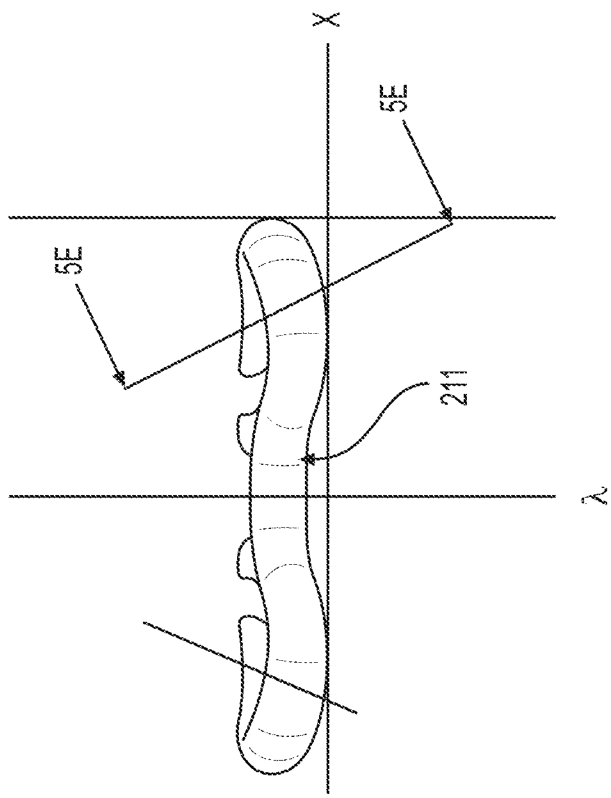
FIG. 5B is a side view of the cervical plate assembly of FIG. 5A.
Figure 5A:
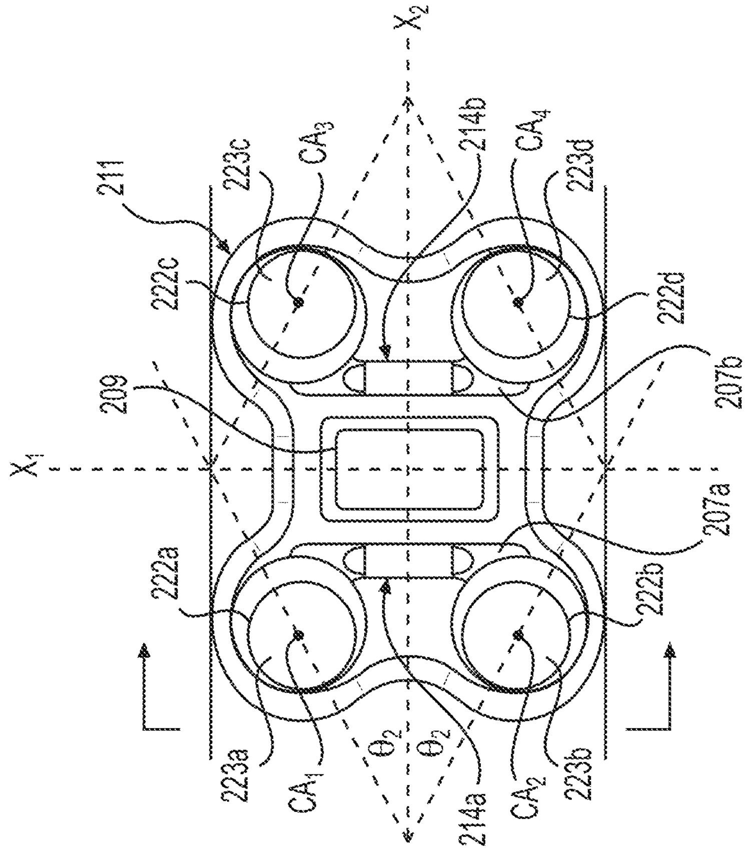
FIG. 5A is a top view of a cervical plate assembly according to one embodiment.
Figure 5C:
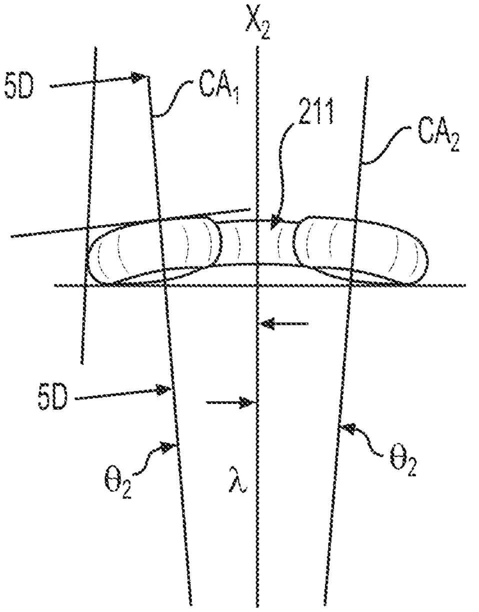
FIG. 5C is a front view of the cervical plate assembly of FIGS. 5A and 5B.
Figure 5D:
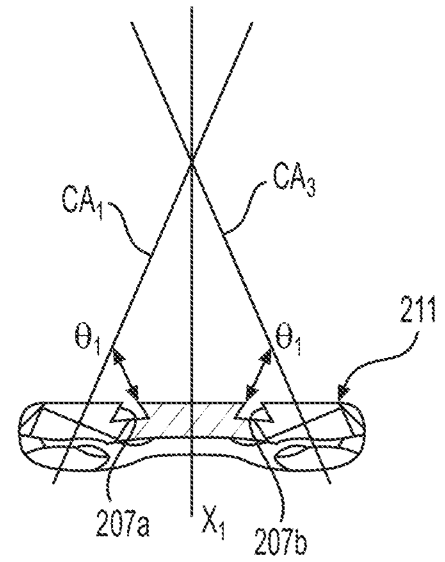
FIG. 5D is a cross-sectional view along line 5D-5D of FIG. 5C.
Figure 5E:
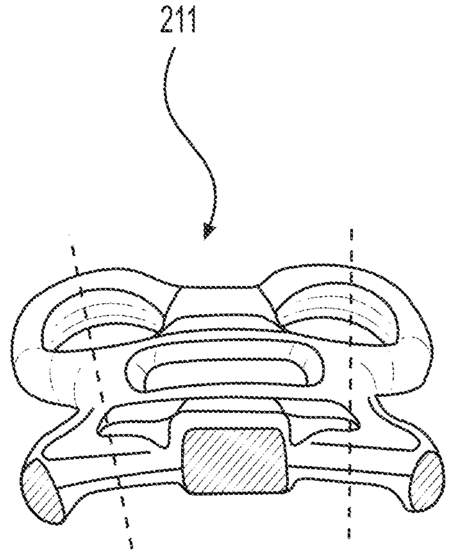
FIG. 5E is a cross-sectional view along line 5E-5E of FIG. 5B.

FIGS. 5A-5E illustrate a base plate 211, and specifically illustrate the relatively high angulation of the bone screw seats 222*a*-222*d*. The base plate 211 includes a central window 209, which can be used by a surgeon during installation to view the disc space (and interbody implant). This window 209 can be used to assist in making sure the base plate 211 is the correct position. Although the window 209 is only illustrated in the embodiment of FIGS. 5A-5E, one of ordinary skill in the art would recognize from the present disclosure that the window 209 can be integrated into the design of any of the base plates disclosed herein. The plate 211 includes two blocking mechanisms 214*a*, 214*b*. As shown in FIG. 5A, the plate 211 defines channels 207*a*, 207*b* for each of the blocking mechanisms 214*a*, 214*b* in which blocking elements can slide. Blocking elements (not shown in FIG. 5A) are retained within the channels 207*a*, 207*b* and are driven outward to the bone screw seats 222*a*-222*d* to retain bone screws with the plate 211. A tapered profile defined by the channels 207*a*, 207*b* is shown in FIG. 5D. The blocking elements of the blocking mechanism 214*a*, 214*b* have a complementary profile such that the blocking elements are retained in the channels 207*a*, 207*b* and can slide within the channels 207*a*, 207*b*. The channels 207*a*, 207*b* define a laterally outer stop surface for the blocking elements.

As shown in FIG. 5A, the base plate 211 is divided by two primary axes: a central lateral axis $X_1$ and a central longitudinal axis $X_2$. The high angulation of the bone screw seats 222*a*-222*d* provides a strong and rigid construction for attaching bone screws to a patient. The plate 211 allows bone screws to be inserted at high cephalad and caudal angles. The high angulation also allows for longer bone screws to be used for implantation, which corresponds to increased mechanical purchase and improved strength of the implantation. Each of the bone screw seats 222*a*-222*d* define a borehole 223*a*-223*d* with a central axis $CA_1$-$CA_4$. Each central axis $CA_1$-$CA_4$ of boreholes 223*a*-223*d* is angled relative to the central lateral axis $X_1$ of the base plate 211 at a first angle $\theta_1$. In one embodiment, the first angle $\theta_1$ is between 50-75 degrees. In one embodiment, the first angle $\theta_1$ is at least 65 degrees. In one embodiment, the first angle $\theta_1$ is at least 70 degrees. Each central axis $CA_1$-$CA_4$ of boreholes 223*a*-223*d* is also angled relative to the central longitudinal axis $X_2$ at a second angle $\theta_2$. In one embodiment, the second angle $\theta_2$ is between 4-8 degrees. In one embodiment, the second angle $\theta_2$ is at least 6 degrees. Both the first angle $\theta_1$ and the second angle $\theta_2$ can be varied depending on the type of bone screw being used in a particular assembly. During installation, the threaded ends of bone screws inserted into bone screw seats 223*a* and 223*b* (with respect to the view shown in FIG. 5A) are angled or canted towards each other on an underside of the base plate 211 due to the second angle $\theta_2$. Although the angulation of the central axes $CA_1$-$CA_4$ of the boreholes 223*a*-223*d* for the bone screw seats 222*a*-222*d* are only specifically illustrated in FIGS. 5A-5E and explained with respect to these figures, one of ordinary skill in the art would understand that these angulation values are present for any of the other embodiments of the base plate described herein.

Figure 6A:
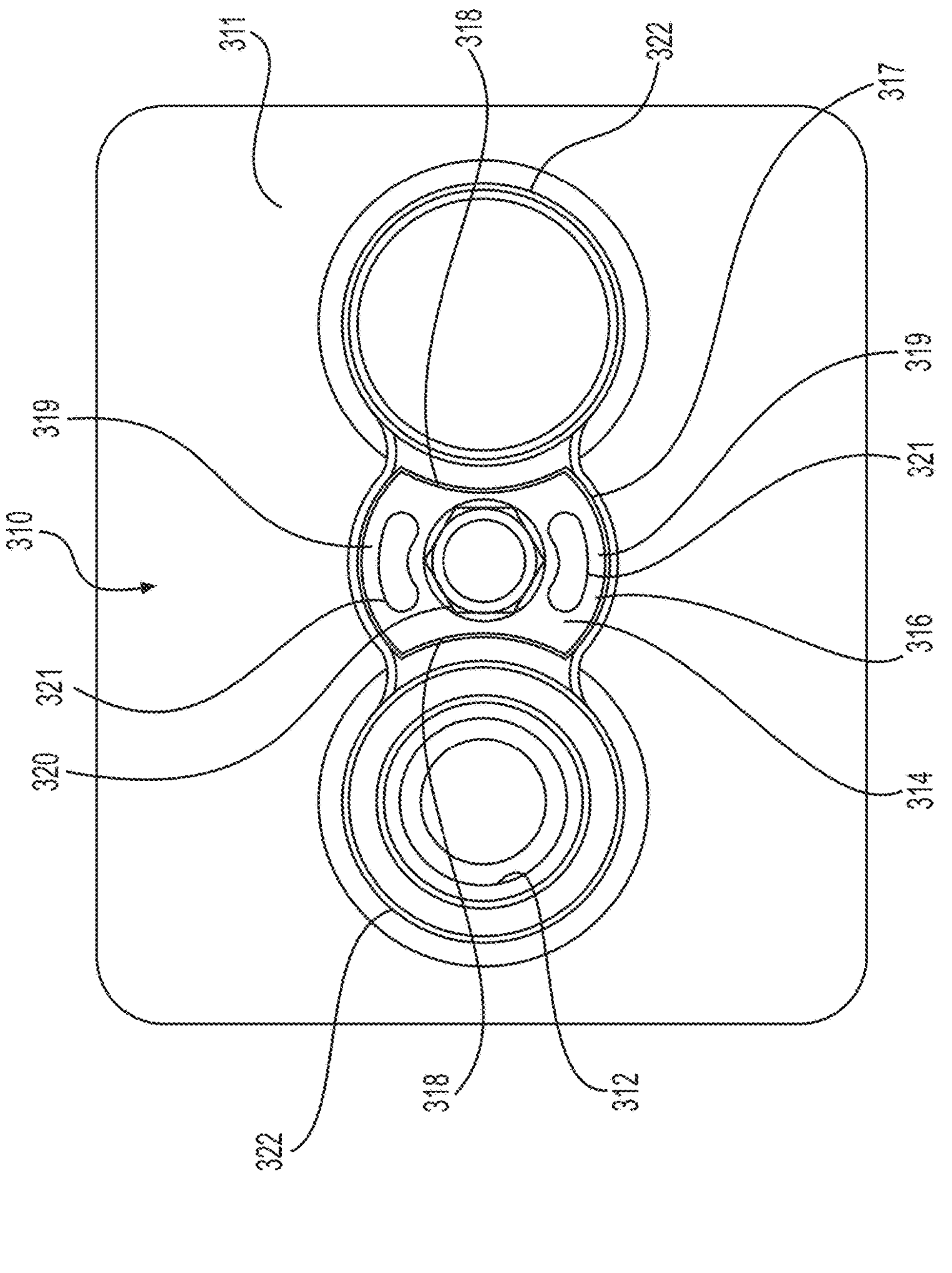
FIG. 6A is a top view of a cervical plate assembly in an open position according to one embodiment.
Figure 6B:
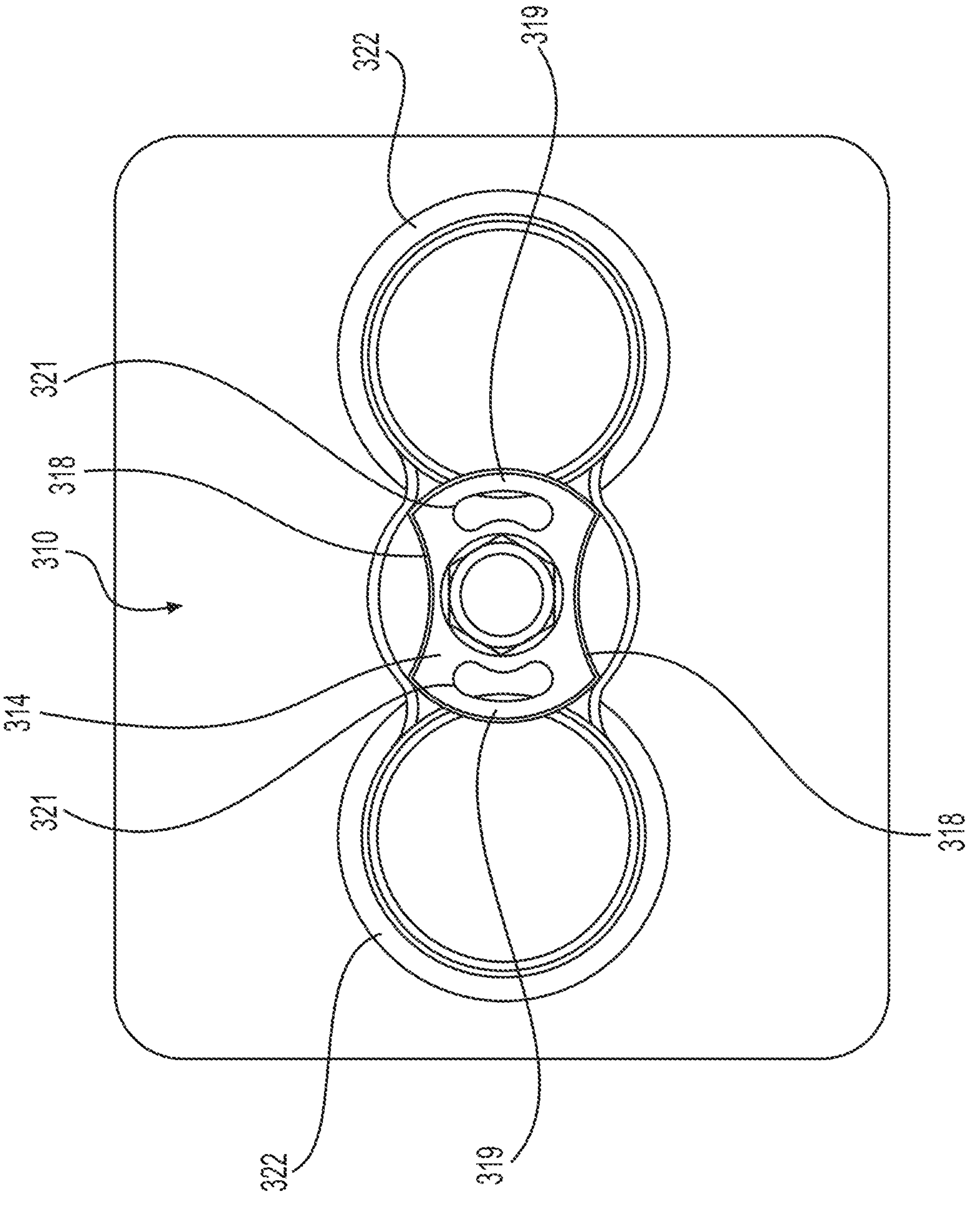
FIG. 6B is a top view of the cervical plate assembly of FIG. 6A in a blocked position.
Figure 6C:
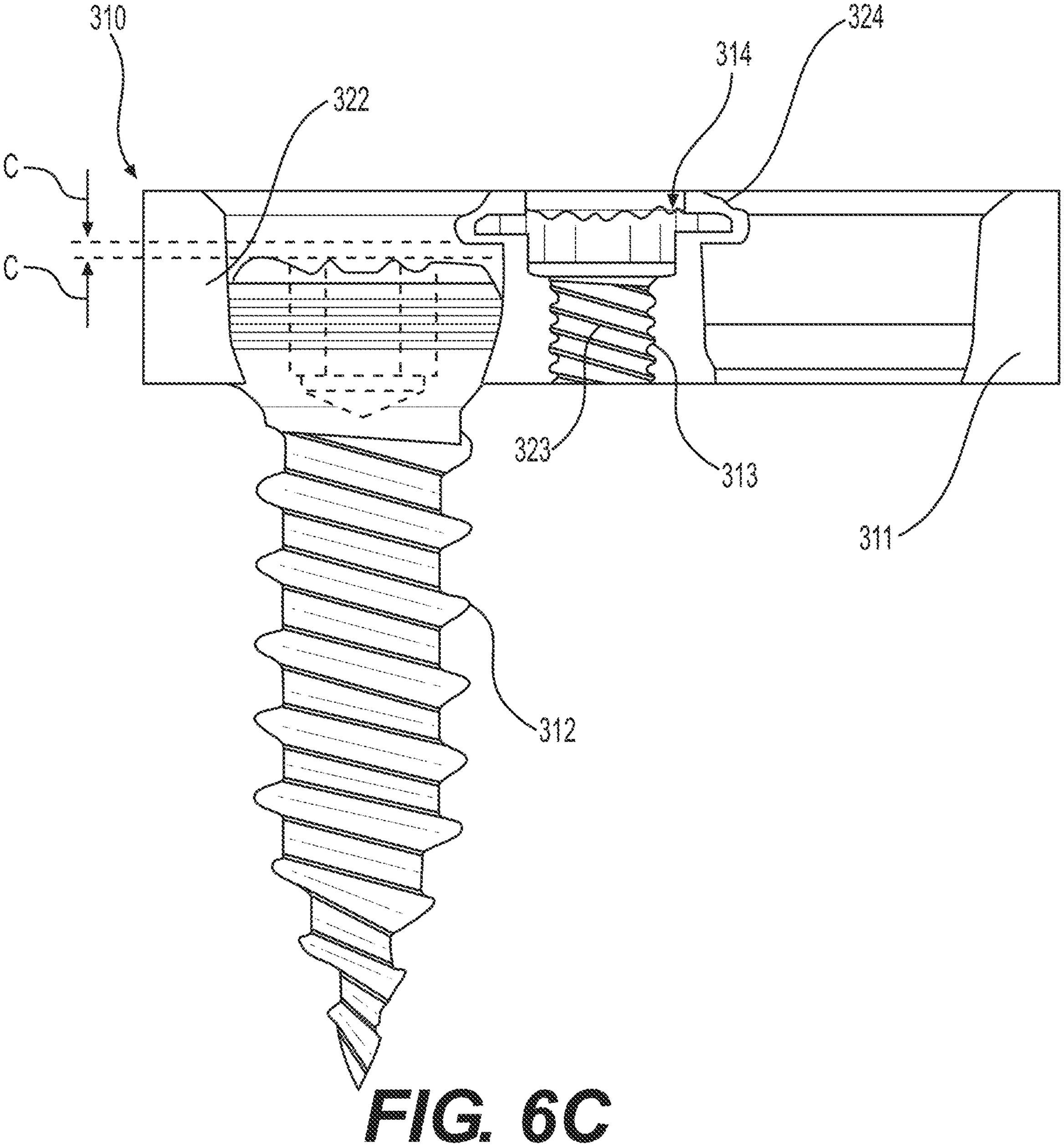
FIG. 6C is a side cross sectional view of the cervical plate assembly of FIGS. 6A and 6B including a bone screw in a blocked position.

FIGS. 6A-6C illustrate another embodiment of a plate assembly 310 including a base plate 311. As shown in FIGS. 6A-6C the plate assembly 310 includes two bone screw seats 322, with a single bone screw 312 arranged in one of the bone screw seats 322. This plate assembly 310 is only illustrated with two bone screw seats 322, but one of ordinary skill in the art would understand that the features of this embodiment can be adapted for a plate assembly including any number of bone screw seats. This plate assembly 310 is also illustrated as having a generic rectangular profile, however one of ordinary skill in the art would understand that the profile of the plate itself can vary, and can resemble the profile of the base plate 11 described above.

The plate assembly 310 includes a blocking mechanism 314 having a different profile than the blocking mechanisms 14*a*, 14*b* of FIGS. 1-3B. The blocking mechanism 314 includes a head 316 with a varying circumferential edge 317, and an engagement recess 320 configured to engage a tool for rotationally driving the blocking mechanism 314. The edge 317 includes diametrically opposed cutouts 318, and diametrically opposed lobes 319. The cutouts 318 are dimensioned to allow insertion of the bone screw 312, and the lobes 319 are configured to block the bone screw 312 from backing out of the plate assembly 310. The lobes 319 are also configured to deflect inward when the bone screw is inserted and then blocks the bone screw from backing out. The circumferential edge 317 of the blocking mechanism 314 has a symmetrical profile such that the blocking mechanism 314 provides an identical profile if the blocking mechanism 314 is rotated 180°. Slots 321 are provided on the blocking mechanism 314 which provide grips or insertion points for a tool for rotating the blocking mechanism 314. FIG. 6A illustrates the blocking mechanism 314 in an open position, and FIG. 6B illustrates the blocking mechanism 314 in a blocked position without a bone screw 312. FIG. 6C illustrates a side cross section view of the plate assembly 310. As shown in FIG. 6C, the plate 311 defines a blocking mechanism seat 324 which axially retains the blocking mechanism 314 within the plate 311. The plate 311 defines grooves 313 configured to engage a threading 323 defined on the blocking mechanism 314. It should be noted that, a bone screw can be inserted into screw holes even when the blocking mechanism 314 is in a blocked position as shown in FIG. 6B, as the lobes of the blocking mechanism may be deformable. As shown in FIG. 6C, a clearance (c) is defined between the blocking mechanism 314 and the bone screw 312 when the bone screw 312 is fully seated in the bone screw seat 322. Although the clearance (c) is only illustrated with respect to this embodiment, one of ordinary skill in the art would recognize that the clearance can be provided in any of the other embodiments described herein.

Figure 7A:
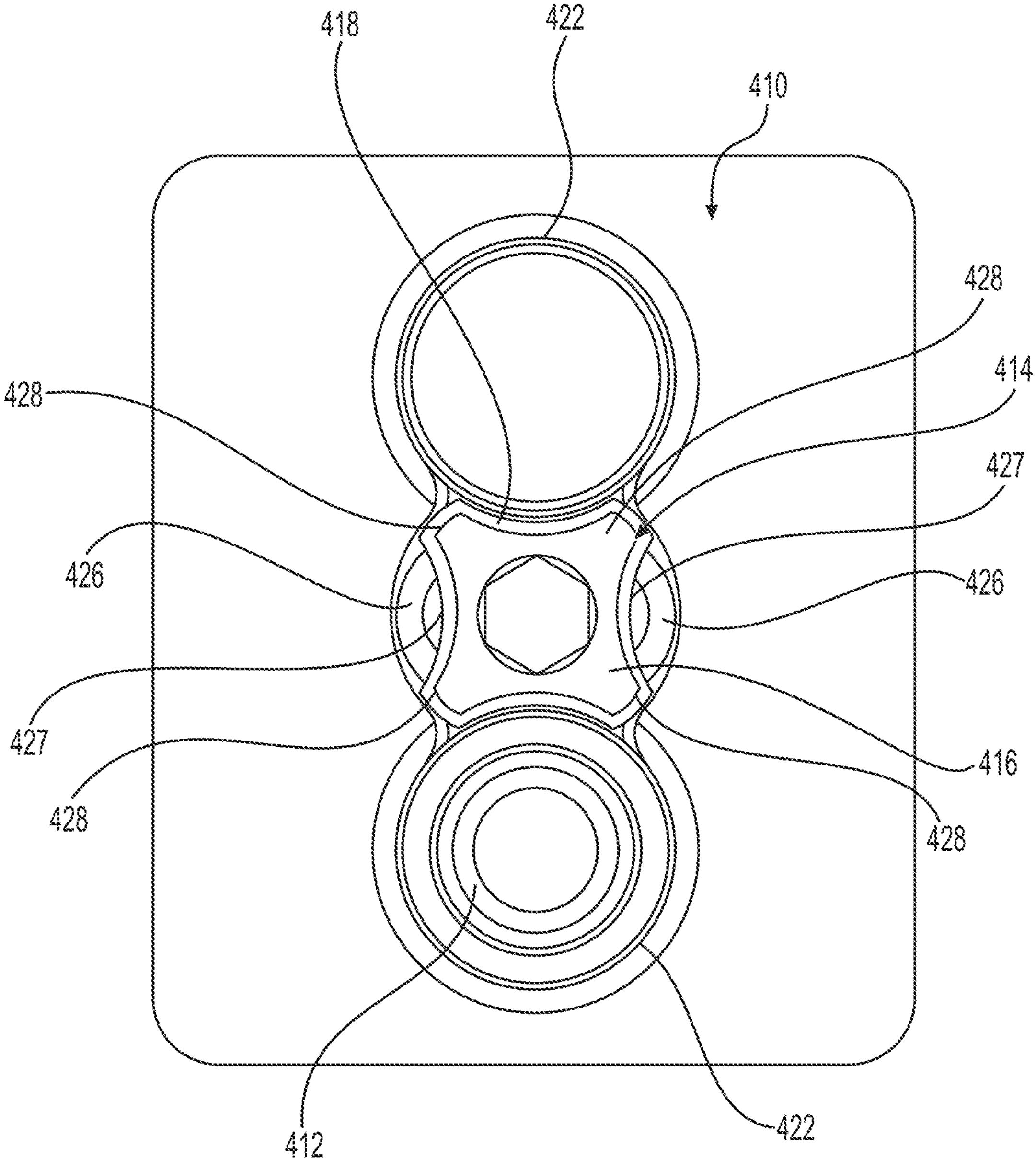
FIG. 7A is a top view of a cervical plate assembly in an open position according to one embodiment.
Figure 7B:
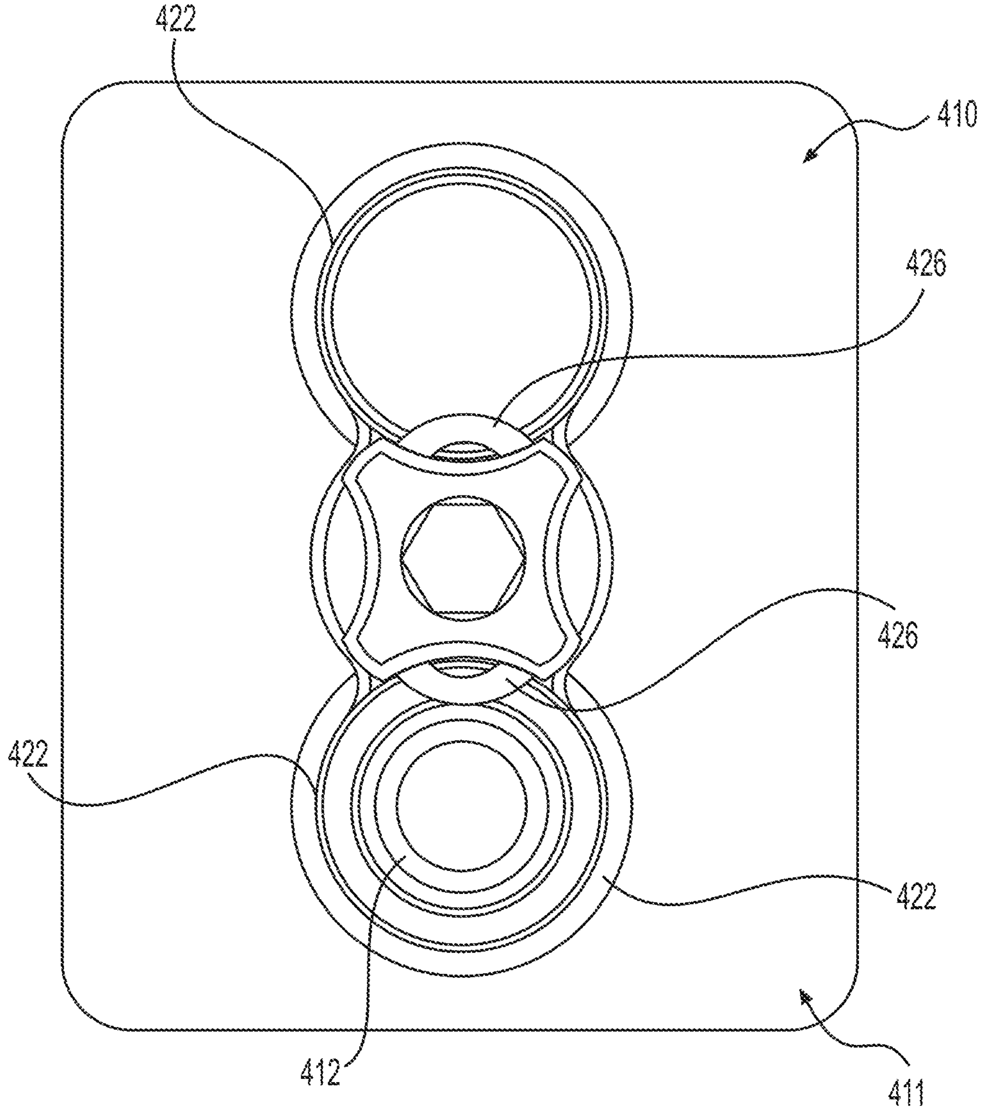
FIG. 7B is a top view of the cervical plate assembly of FIG. 7A in a blocked position.
Figure 7C:
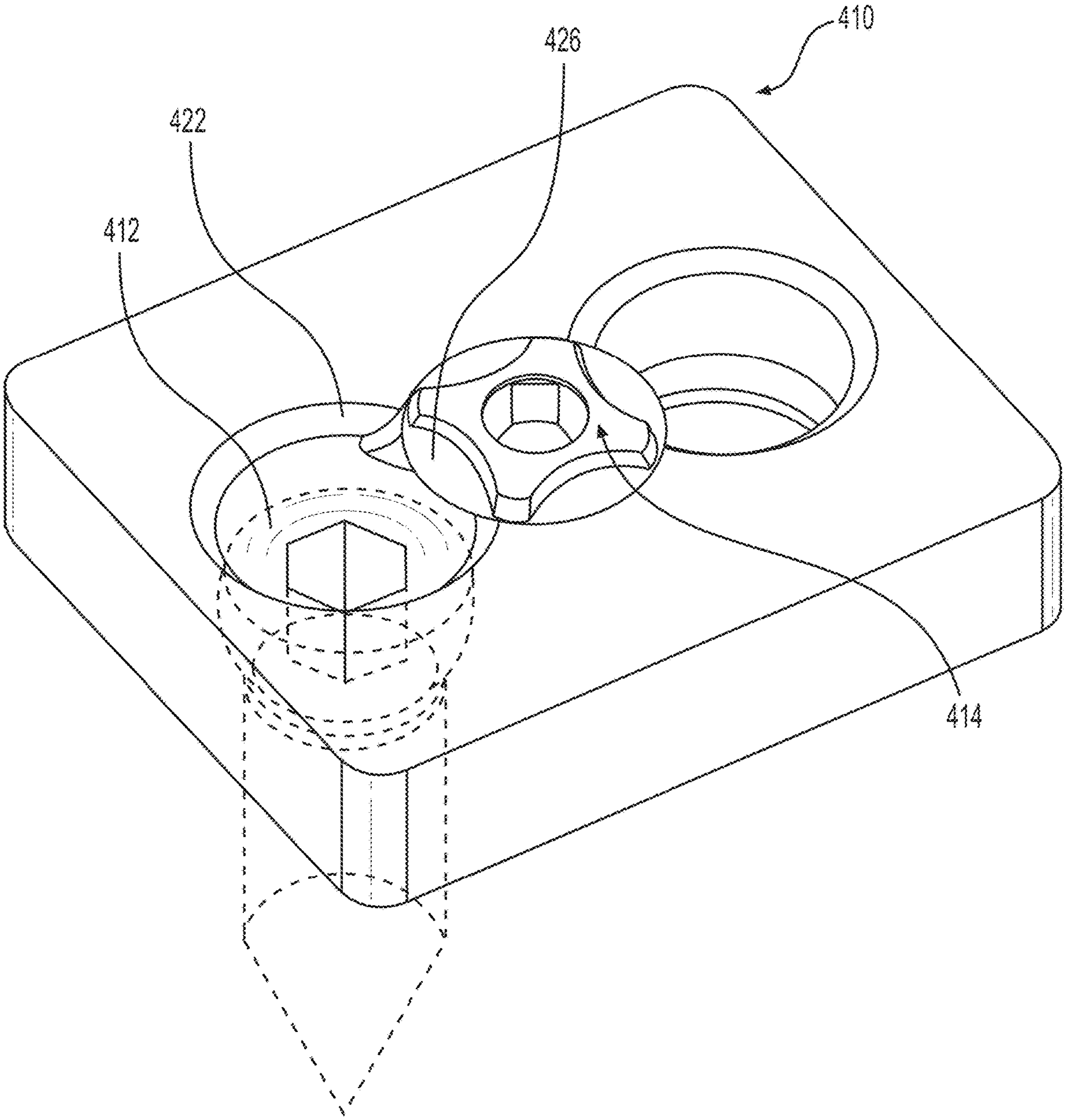
FIG. 7C is a perspective view of the cervical plate assembly of FIGS. 7A and 7B in the blocked position.
Figure 7D:
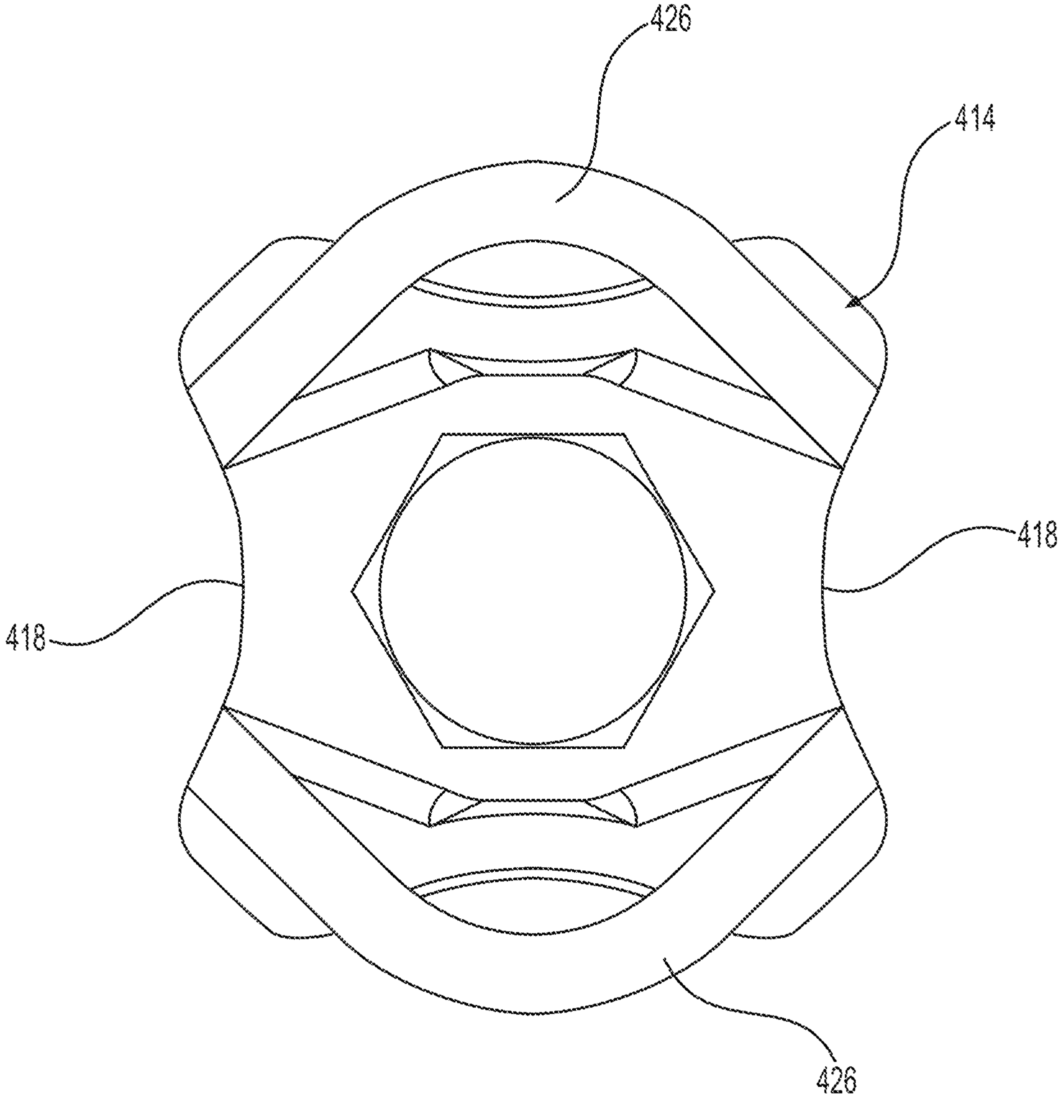
FIG. 7D is a cross section view of a blocking mechanism of the cervical plate assembly of FIGS. 7A-7C.

FIGS. 7A-7D illustrate another embodiment of a plate assembly 410 and a base plate 411. The blocking mechanism 414 includes a head 416 having a generally X-shaped profile, and including four arms 428. Resilient blocking elements 426 extend between a respective pair of the four arms 428 on diametrically opposed sides of the head 416. Reliefs 427 are provided on sides of the head 416 including the resilient blocking elements 426. These reliefs 427 allow for the resilient blocking elements 426 to deform radially inwardly towards a central rotational axis of the blocking mechanism 414. FIG. 7A illustrates the blocking mechanism 414 in an open position. FIG. 7B illustrates the blocking mechanism 414 is a blocked position, with the resilient blocking elements 426 overlapping the bone screw seats 422. This particular blocking mechanism 414 can be in either the open or blocked position and still allow insertion of the bone screw 412 into the plate assembly 410. This embodiment allows for the bone screw 412 to be inserted into the plate assembly 410 when the blocking mechanism 414 is in the blocked position (FIG. 7B) due to clastic deformation of the resilient blocking elements 426 during insertion of the bone screw 412. Once fully inserted and installed, the bone screw 412 is prevented from backing out of the plate assembly 410 due to the resilient blocking elements 426. In one embodiment, the resilient blocking element 426 is formed from spring steel. In another embodiment, the resilient blocking element 426 is formed from an elastomeric material. One of ordinary skill in the art would recognize from the present disclosure that alternative types of blocking elements 426 can be used as long as the blocking elements 426 are configured to elastically deform during insertion of the bone screws and return to an initial position after insertion that blocks or overlaps with the inserted bone screw. FIG. 7C illustrates the plate assembly 410 in a perspective view with the blocking mechanism 414 in a blocked position. As shown more clearly in FIG. 7D, the blocking mechanism 414 includes cutouts 418 that are dimensioned to allow passage of the bone screws 412.

Figure 8:
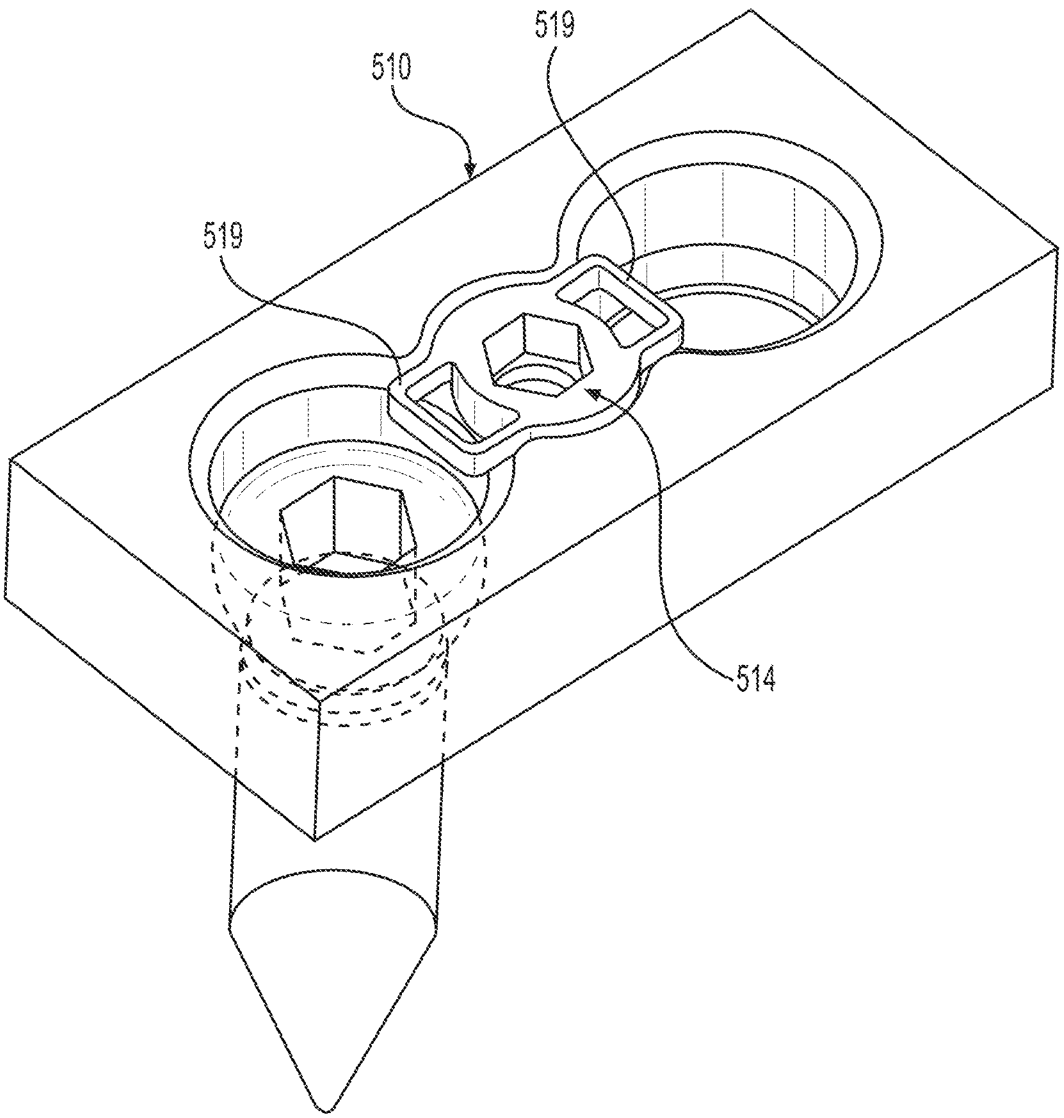
FIG. 8 is a perspective view of a cervical plate assembly in a blocked position according to one embodiment.
Figure 9A:
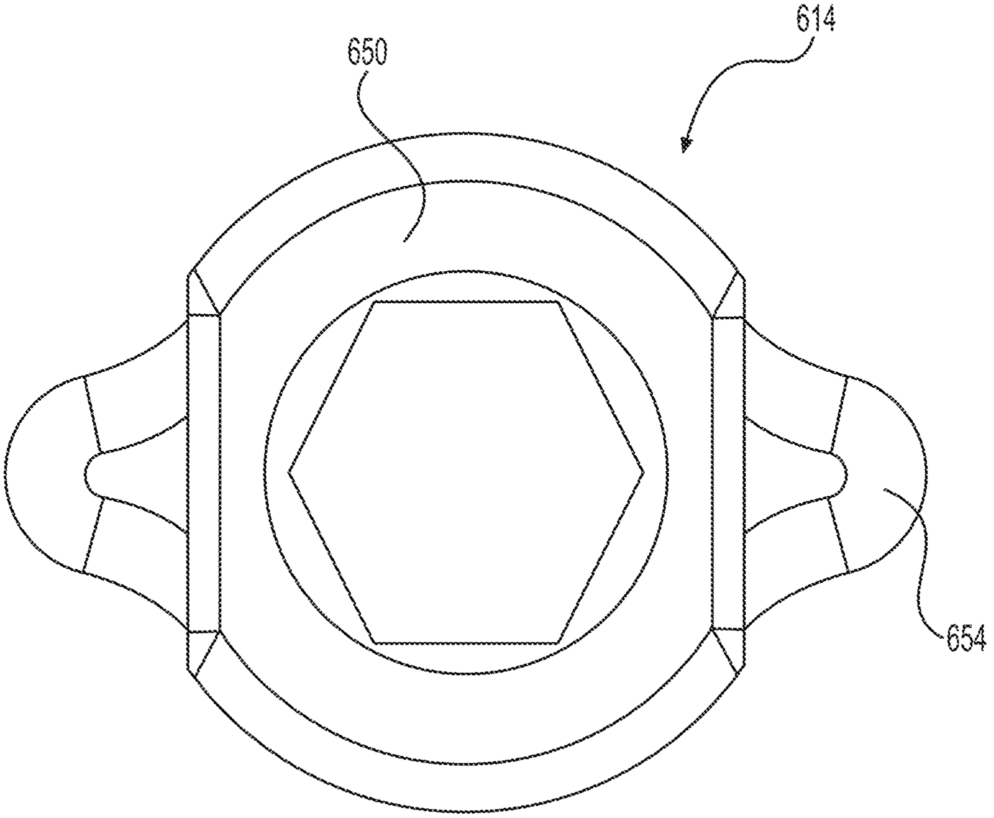
FIG. 9A is a top view of a blocking mechanism according to one embodiment.
Figure 9B:
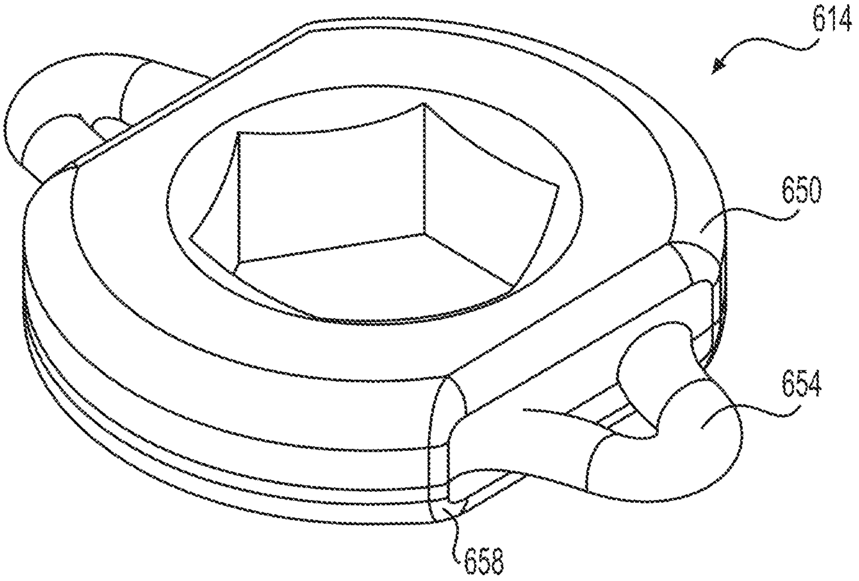
FIG. 9B is a perspective view of the blocking mechanism of FIG. 9A.
Figure 9C:
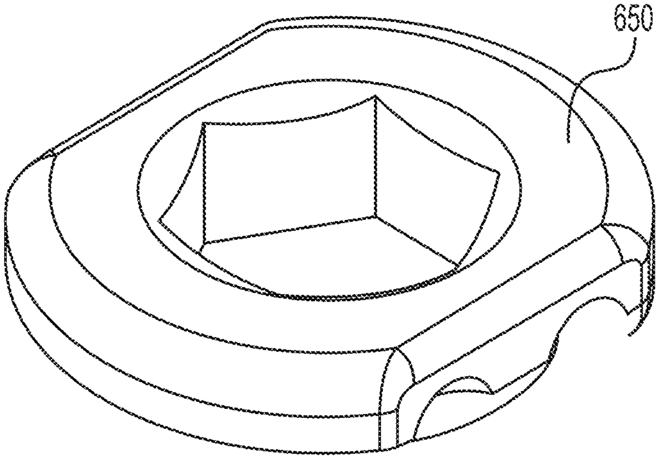
FIGS. 9C-9E are perspective views of sub-components of the blocking mechanism of FIGS. 9A and 9B.
Figure 9D:
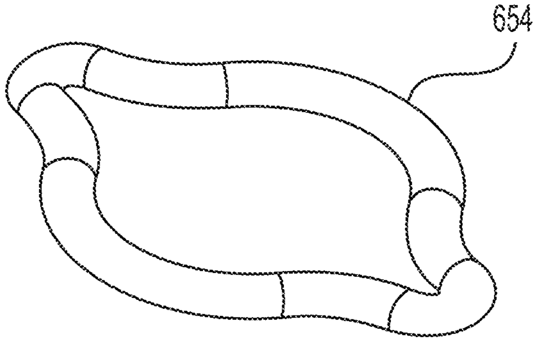
Figure 9E:
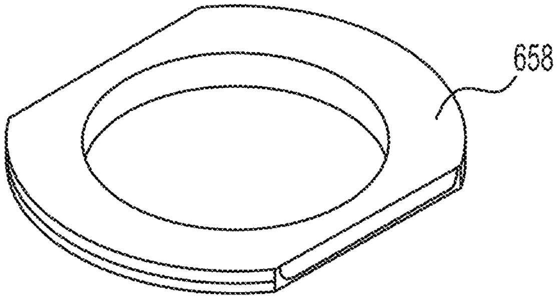

FIG. 8 illustrates another embodiment of a plate assembly 510 in a blocked position. The plate assembly 510 includes a blocking mechanism 514 including blocking lobes 519. The blocking lobes 519 may have a rectangular profile. One of ordinary skill in the art would recognize from the present disclosure that the profile of the lobes can be modified.

FIGS. 9A-9E illustrate another embodiment of a blocking mechanism 614. The blocking mechanism 614 of FIGS. 9A-9E can be integrated into any of the plate assemblies described herein. The blocking mechanism 614 includes a hub 650, a blocking element 654, and retention washer 658. The hub 650 defines grooves for accommodating the blocking element 654. The blocking element 654 defines lobes on diametrically opposite sides of the blocking element 654, each configured to block a bone screw within a cervical plate assembly. The blocking element 654 can be formed as a wire forming a continuous loop. The blocking element 654 can be snapped into or placed into the grooves formed on the hub 650, and a retention washer 658 can then be pressed or snapped onto a bottom end of the hub 650. The retention washer 658 can be snapped into a groove formed on the hub 650 such that the blocking element 654 is retained between the hub 650 and the retention washer 658. The blocking mechanism 614 can be rotated while retained within a seat of a base plate, such that the blocking element 654 moves from a position overlapping with a bone screw seat to block the bone screw seat, to an open position in which the blocking element 654 is rotated away from the bone screw seat and the bone screw seat is unobstructed.

Figure 10A:
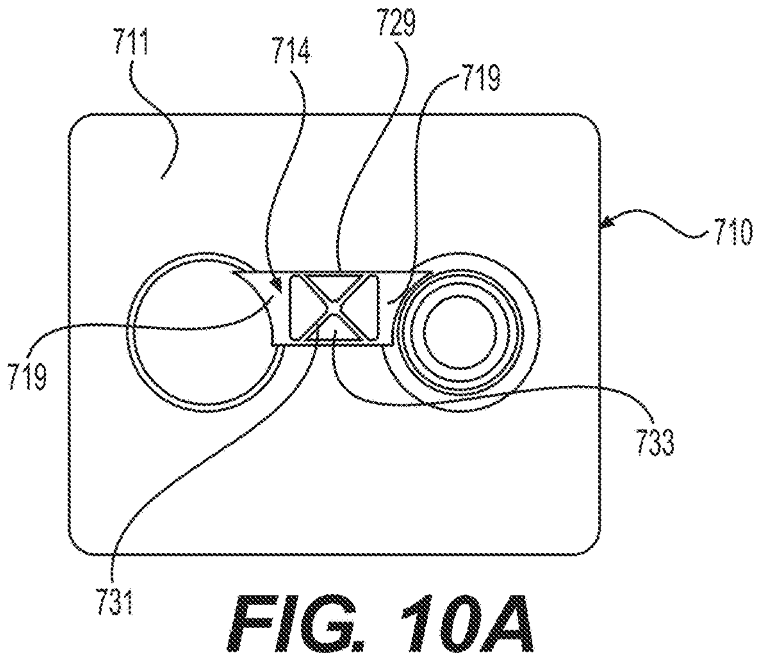
FIG. 10A is a top view of a cervical plate assembly including a bone screw in a blocked position according to one embodiment.
Figure 10B:
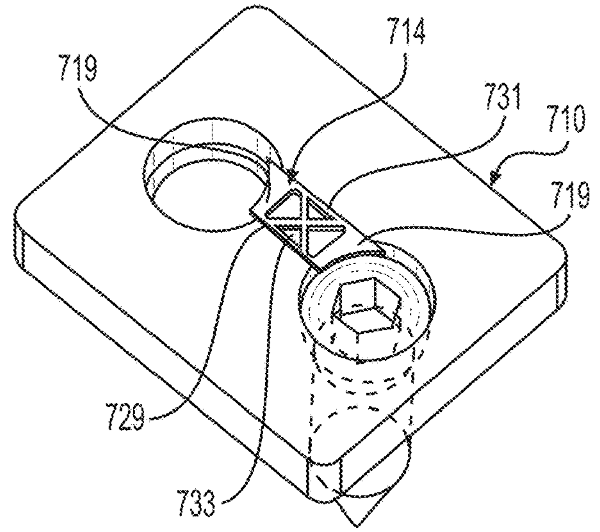
FIG. 10B is a perspective view of the cervical plate assembly of FIG. 10A.
Figure 10C:
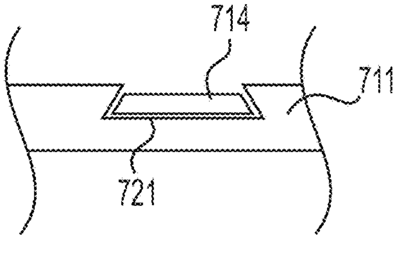
FIG. 10C is a side cross section view of the base plate of FIGS. 10A and 10B.

FIGS. 10A-10C illustrate another embodiment of a plate assembly 710. The plate assembly 710 includes a blocking mechanism 714 including blocking tabs 719 arranged on opposite sides of a central portion 729. The blocking tabs 719 are configured to provide obstructions to an underlying bone screw seat, such that a bone screw is retained with the plate assembly 710. The central portion 729 includes resilient arms 731, such that the blocking mechanism 714 can be deformed by applying inward pressure to the blocking tabs 719. The resilient arms 731 form an X-shaped configuration with reliefs 733 formed between the arms 731. A user can manually pinch the blocking tabs 719 towards each other, and the blocking mechanism 714 can be manipulated from an open position to a blocked position without the use of a tool. The blocking mechanism 714 can be retained with the base plate 711 via a slot 721 formed in the base plate 711, or other retention configuration. As shown in FIG. 10C, the slot 721 has a tapered profile, and the blocking mechanism 714 has a complementary tapered profile such that the blocking mechanism 714 is retained within the slot 721. One of ordinary skill in the art would understand from the present disclosure that this slot 721 can be integrated into any of the base plates described herein to retain a blocking mechanism.

Figure 11A:
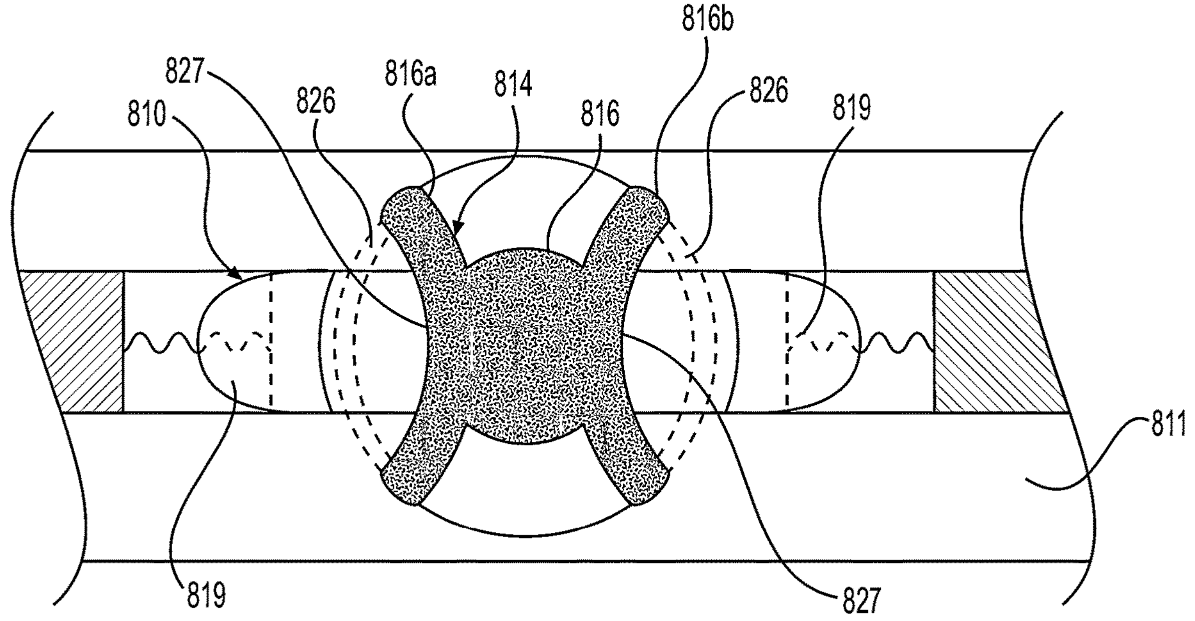
FIG. 11A is a top view of an embodiment of a cervical plate assembly.
Figure 11B:
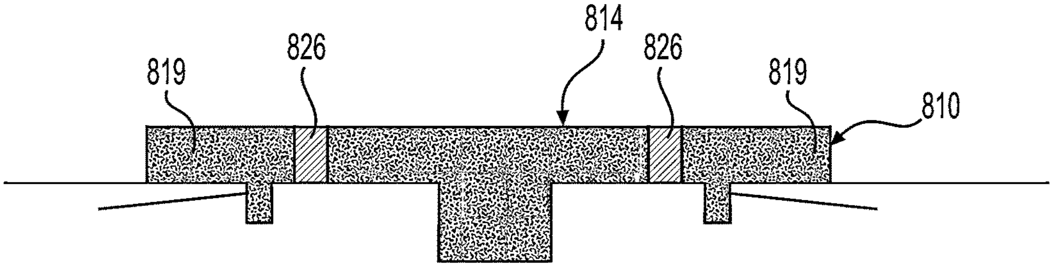
FIG. 11B is a side view of the cervical plate assembly of FIG. 11A.

FIGS. 11A and 11B illustrate another embodiment of a plate assembly 810 including a blocking mechanism 814. The blocking mechanism 814 includes a central hub 816 defining a pair of C-shaped arms 816a, 816b, with resilient blocking elements 826 extending therebetween. Blocking tabs 819 are engaged against a respective one of the resilient blocking elements 826. Reliefs 827 are formed on the hub 816, and the reliefs 827 are dimensioned to each accommodate one of the resilient blocking elements 826 and one of the blocking tabs 819. FIG. 11A illustrates the blocking mechanism 814 in an expanded state in which the blocking tabs 819 are extended and configured to block a bone screw seat. The blocking mechanism 814 is configured to be rotated by 90° such that the blocking tabs 819 and the resilient blocking elements 826 are pushed inwardly into a respective one of the reliefs 827, and the blocking tabs 819 and the resilient blocking elements 826 are in a compressed state. The blocking tabs 819 can be retained within slots formed in the base plate 811, such that the blocking tabs 819 slide within the slots.

Figure 12:
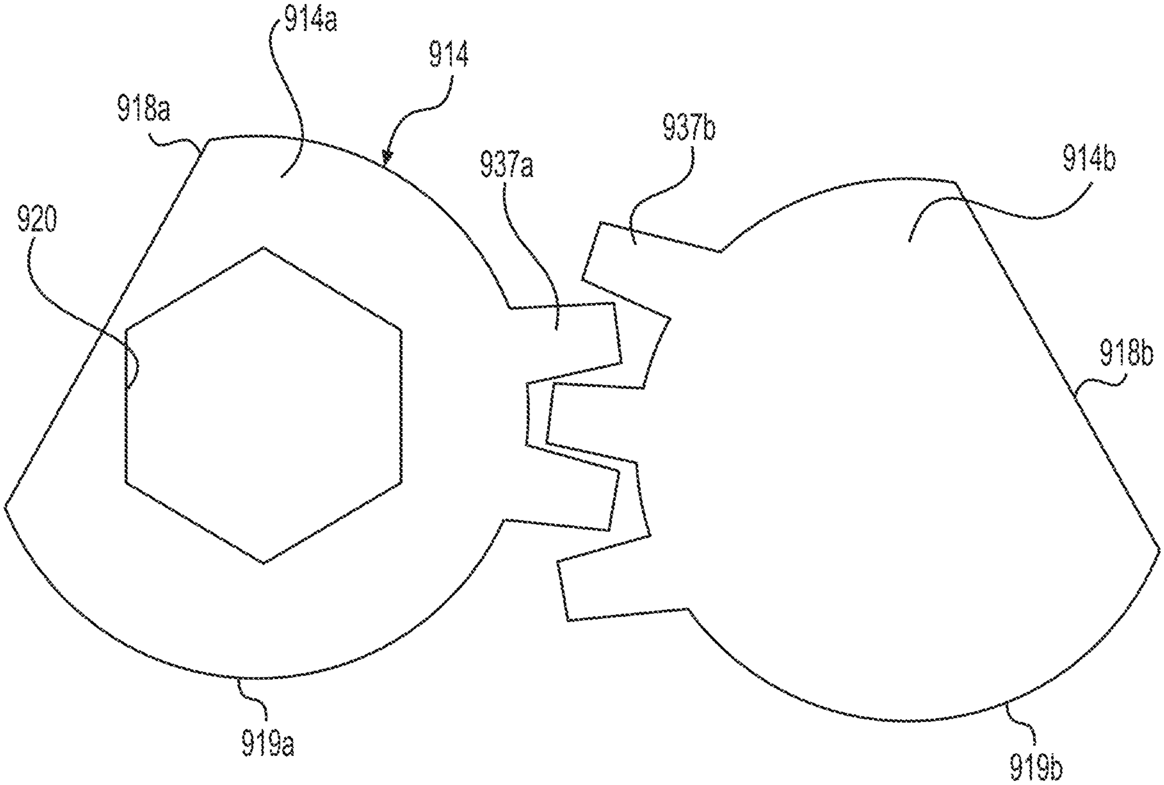
FIG. 12 is a top view of an embodiment of a blocking mechanism.

FIG. 12 illustrates an alternative configuration for a blocking mechanism 914 in which two blocking screws 914a, 914b are provided for blocking a respective bone screw seat. As shown in FIG. 12, a single blocking screw 914a includes an engagement recess 920 configured to be engaged by a tool to rotate the blocking screw 914a. Each of the blocking screws 914a, 914b include teeth 937a, 937b which engage each other such that rotation of the first blocking screw 914a drives rotation of the second blocking screw 914b. The blocking screws 914a 914b each define a blocking lobe 919a, 919b and a cutout 918a, 918b such that in a blocked position the blocking lobes 919a, 919b overlap with a bone screw seat, and in an open position the cutouts 918a, 918b overlap with a bone screw seat to allow for insertion of a bone screw.

Figure 13:
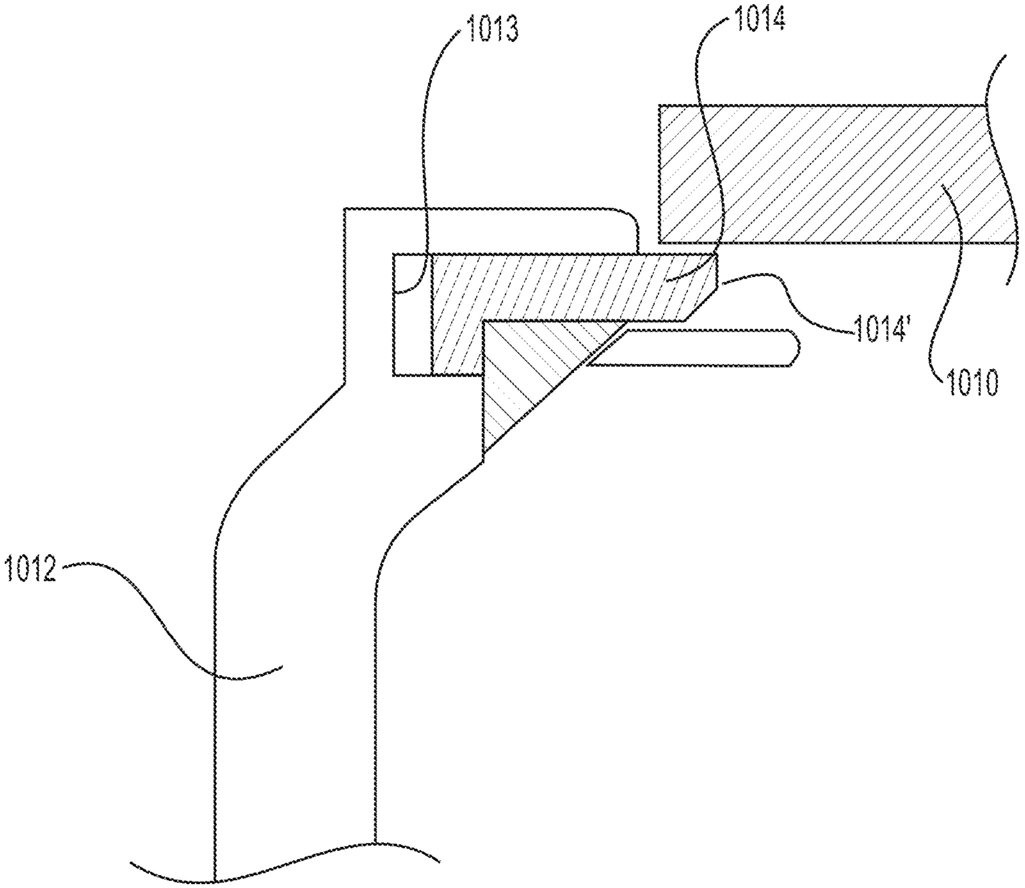
FIG. 13 is a side view of an embodiment of a blocking mechanism associated with a bone screw.

FIG. 13 illustrates a blocking mechanism 1014 that is directly integrated with a bone screw 1012. As shown in FIG. 13, the bone screw 1012 is inserted into a base plate 1010, and the blocking mechanism 1014 provides axial retention of the bone screw 1012 relative to the base plate 1010. The blocking mechanism 1014 is formed as a split ring element, which is retained within a groove 1013 formed in a head of the bone screw 1012. A tool including a sleeve can be inserted around the head of the bone screw 1012 to push the blocking mechanism 1014 into the groove 1013 of the bone screw 1012. The blocking mechanism 1014 can define a tapered edge 1014' which is configured to engage against the base plate 1010 during insertion, such that the tapered edge 1014' slides along the base plate 1010 and the blocking mechanism 1014 is pushed into the groove 1013.

Figure 14A:
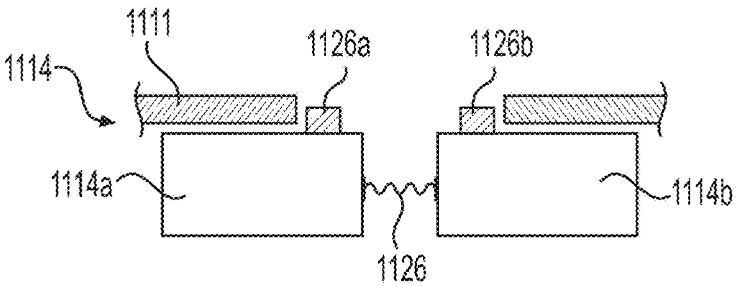
FIG. 14A is a side view of a blocking mechanism according to one embodiment in an open position.
Figure 14B:
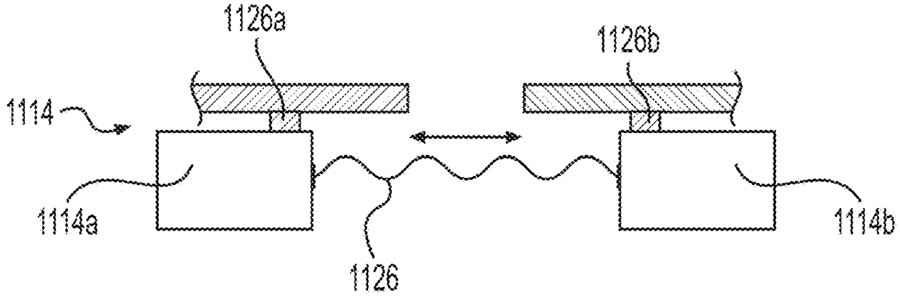
FIG. 14B is a side view of the blocking mechanism of FIG. 14A in a blocked position.
Figure 14C:
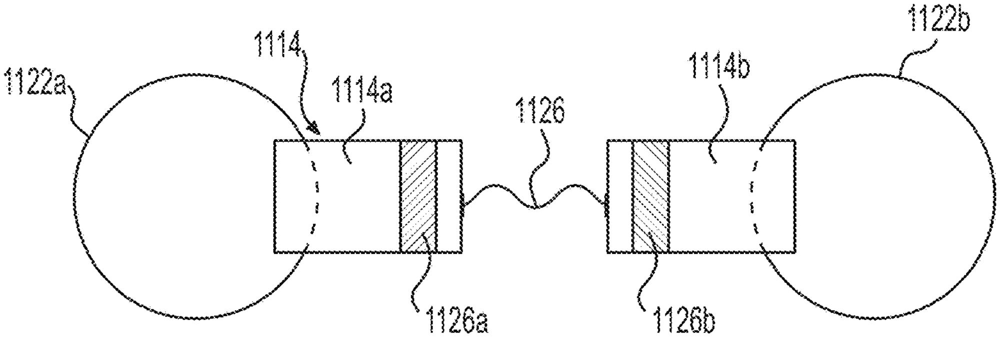
FIG. 14C is a top view of the blocking mechanism of FIGS. 14A and 14B.
Figure 14D:
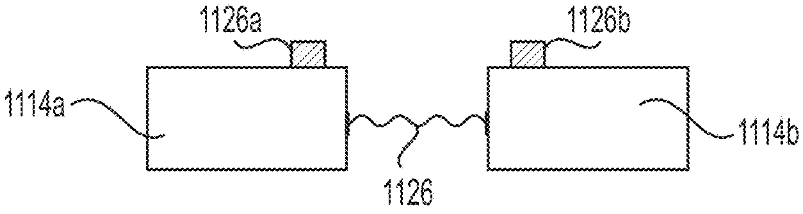
FIG. 14D is a side view of a portion of the blocking mechanism of FIGS. 14A-14C.

FIGS. 14A-14D illustrate a blocking mechanism 1114 including two blocking elements 1114a, 1114b, a central resilient element 1126, and two blocking resilient elements 1126a, 1126b. As shown in FIG. 14A, the blocking resilient elements 1126a, 1126b are engaged against a base plate 1111, and retain the blocking elements 1114a, 1114b in a first position, which can correspond to an open configuration. The central resilient element 1126 biases the blocking elements 1114a, 1114b outward from each other, but the blocking resilient elements 1126a, 1126b define a stop against the base plate 1111 and prevent this outward movement in FIG. 14A. As shown in FIG. 14B, once the blocking resilient elements 1126a, 1126b are downwardly depressed, then the central resilient element 1126 drives the blocking elements 1114a, 1114b outward to a second position, which can correspond to a blocked position. FIG. 14C shows a top view of the blocking mechanism 1114 with the blocking elements 1114a, 1114b in the blocked position and overlapping the bone screw seats 1122a, 1122b. FIG. 14D illustrates the blocking mechanism 1114 separate from the base plate 1111. In one embodiment, the blocking resilient elements 1126a, 1126b are pressed downward via a tool. One of ordinary skill in the art would recognize that the blocking resilient elements 1126a, 1126b can be pressed downward by a user/surgeon. In one embodiment, the blocking resilient elements 1126a, 1126b are spring elements (e.g., leaf springs, cantilevered springs, etc.), but one of ordinary skill in the art would recognize from the present disclosure that alternative blocking elements can be used.

Figure 15A:
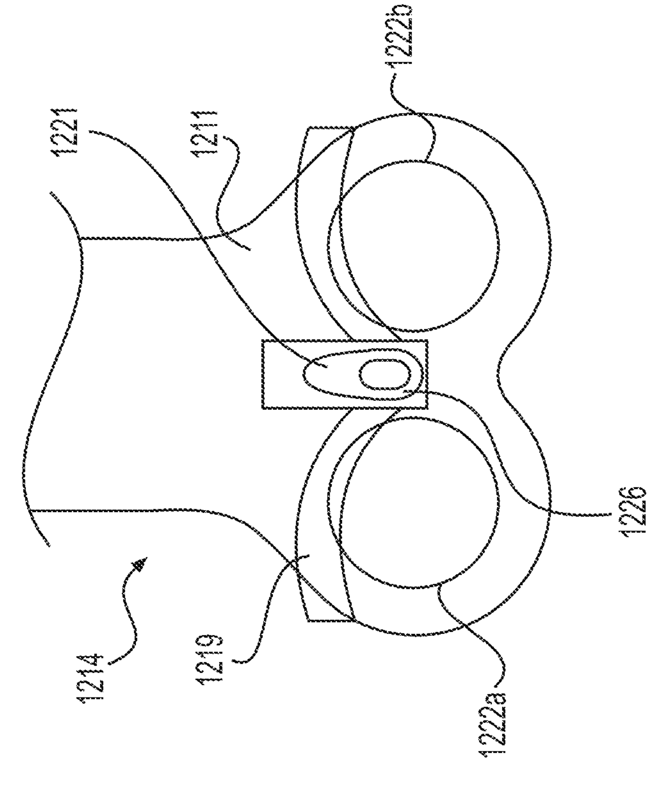
FIG. 15A is a top view of a blocking mechanism according to one embodiment in a blocked position.
Figure 15B:
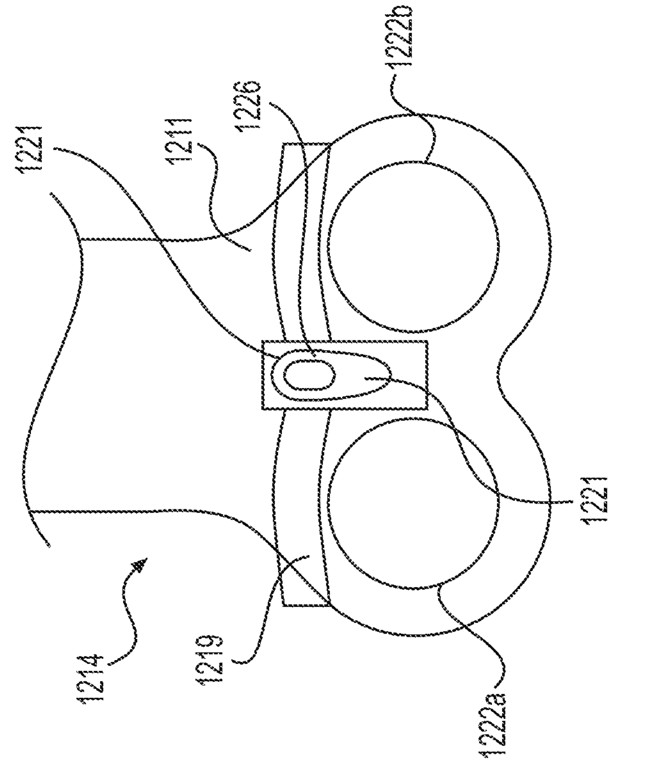
FIG. 15B is a top view of the blocking mechanism of FIG. 15A in an open positon.

FIGS. 15A and 15B illustrate another embodiment of a blocking mechanism 1214. In this embodiment, the blocking mechanism 1214 includes a central blocking element 1219 that moves between a blocked position shown in FIG. 15A and an open position in FIG. 15B in which the bone screw seats 1222a, 1222b are either obstructed (FIG. 15A) or unobstructed (FIG. 15B). The central blocking element 1219 is a flexible plate that extends between lateral sides of the base plate 1211. A blocking cam 1226 is arranged within a slot 1221 formed on the base plate 1211. The blocking cam 1226 is configured to be positioned in a lower position within the slot 1221, as shown in FIG. 15A, in which the central blocking element 1219 is flexed to overlap with the bone screw seats 1222a, 1222b. The terminal ends of the central blocking element 1219 are understood to be fixed to the lateral sides of the base plate 1211 such that the central blocking element 1219 flexes and exhibits inflexion as shown in FIG. 15A. As shown in FIG. 15B, as the blocking cam 1226 is moved upward within the recess 1221, then the central blocking element 1219 returns to a relatively straight profile such that the central blocking element 1219 does not overlap with the bone screw seats 1222*a*, 1222*b*.

Figure 16A:
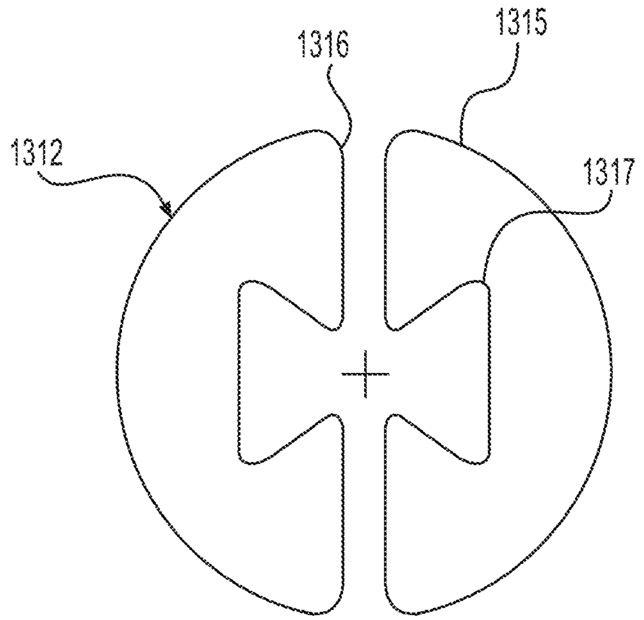
FIG. 16A is a top view of a blocking mechanism according to one embodiment.
Figure 16B:
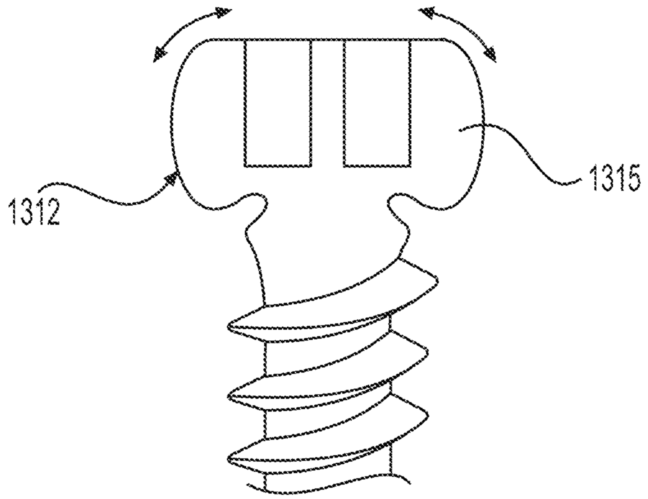
FIG. 16B is a side cross section view of the blocking mechanism of FIG. 16A.

FIGS. 16A and 16B illustrate an alternative embodiment of a bone screw 1312 including a screw head 1315. The screw head 1315 includes a slot 1316 and a relief 1317. The relief 1317 is centered relative to a shaft of the bone screw 1312. The relief 1317 acts as a drive feature to help thread the screw 1312 and allows the screw head 1315 to compress to reduce the outer diameter of the screw head 1315. By having a nominal screw head diameter larger than a bone screw hole diameter defined on the base plate, the screw head 1315 provides an interference fit with the base plate when the driver tool is not engaged. When the bone screw 1312 is fully seated within an associated base plate, and the driver tool is removed from the screw head 1315, then the screw head 1315 expands back open to its nominal diameter, which is oversized relative to the associated bone screw seat and prevents the bone screw 1312 from backing out of the plate. Although an interference type fit is described with respect to this embodiment, one of ordinary skill in the art would recognize from the present disclosure that alternative arrangements could be provided to ensure that the bone screw 1312 has a secure connection to the base plate after insertion. Additionally, although a slot/relief arrangement is described with respect to this embodiment, one of ordinary skill in the art would recognize from this disclosure that alternative geometries can be used to achieve the same result of fixing the bone screw relative to a bone screw seat defined by a base plate.

Figure 17A:
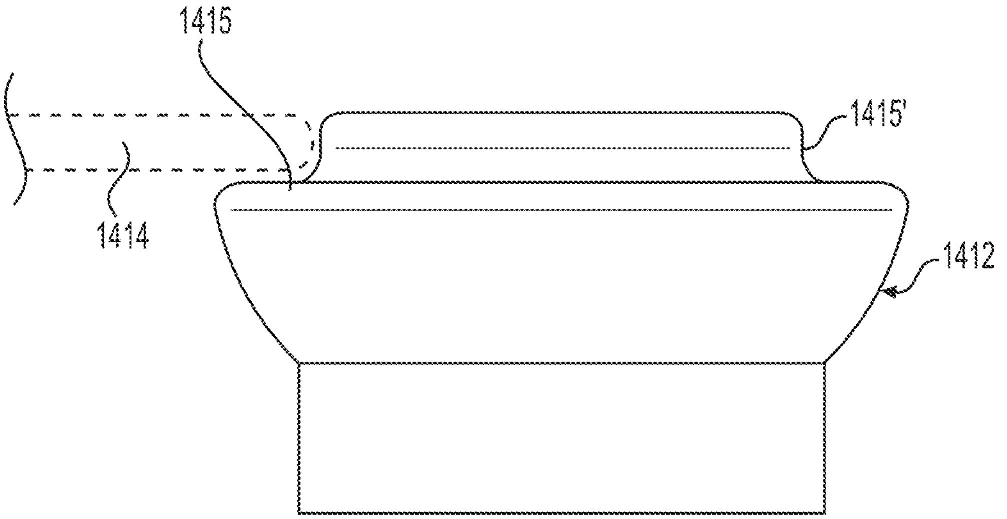
FIG. 17A is a magnified, side view a bone screw according to one embodiment.
Figure 17B:
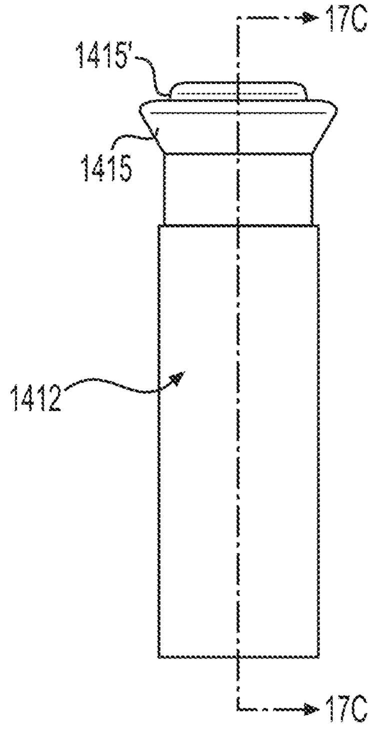
FIG. 17B is a side view of the bone screw of FIG. 17A.
Figure 17C:
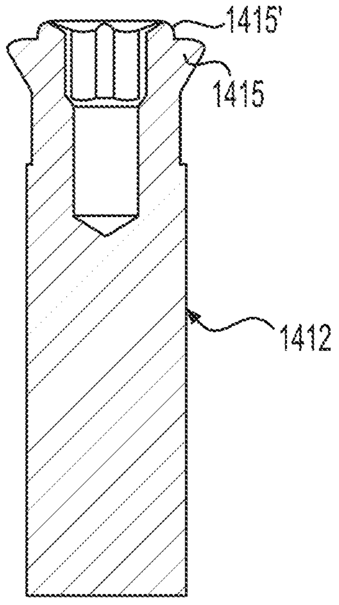
FIG. 17C is a cross section view of the bone screw of FIG. 17B along line 17C-17C.

FIGS. 17A-17C illustrate an alternative embodiment of a bone screw 1412. As shown in FIG. 17A, the bone screw 1412 has a screw head 1415 with a relief 1415'. The relief 1415' is configured to accommodate a portion of a blocking mechanism 1414 (shown in dashed lines in FIG. 17A). This relief 1415' allows for the blocking mechanism to partially overlap an axial end of the bone screw 1412, and as a result allows for a thinner base plate. The relief 1415' also ensures that the blocking mechanism sufficiently overlaps with the bone screw 1412 in the axial direction.

Figure 18C:
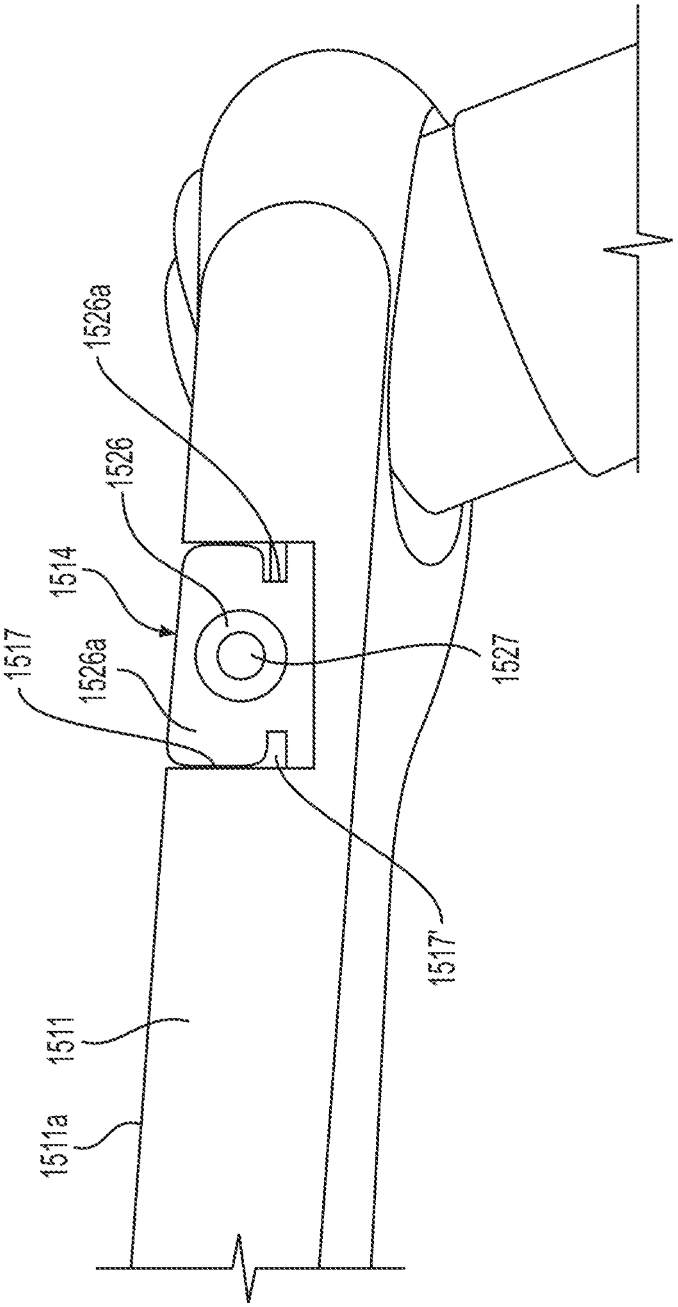
FIG. 18C is a side cross section view of a blocking mechanism for the cervical plate assembly of FIGS. 18A and 18B.

FIGS. 18A-18C illustrate another embodiment of a blocking mechanism 1514. The blocking mechanism 1514 includes a central biasing element 1526 and two blocking elements 1526*a*, 1526*b* on opposite ends of the central biasing element 1526. The blocking mechanism 1514 is retained to a base plate 1511, and the base plate 1511 includes bone screw seats 1522*a*, 1522*b* (a single bone screw 1512 is shown within the base plate 1511). As shown in FIG. 18A, the blocking elements 1526*a*, 1526*b* are in the extended position due to the biasing force from the biasing element 1526. In this position, the blocking elements 1526*a*, 1526*b* overlap with the bone screw seats 1522*a*, 1522*b* and are in a blocked position to retain the bone screws with the base plate 1511. In FIG. 18B, the blocking elements 1526*a*, 1526*b* are in a compressed configuration with the biasing element 1526 being compressed and housed within cavities of the blocking elements 1526*a*, 1526*b*. In this configuration, the blocking elements 1526*a*, 1526*b* are positioned away from the bone screw seats 1522*a* 1522*b* such that the bone screw 1512 can be removed from the base plate 1511. The blocking elements 1526*a*, 1526*b* can be independently moved with respect to each other such that a bone screw 1512 can be removed from one of the bone screw seats 1522*a*, 1522*b* while a bone screw 1512 is blocked in the other one of the bone screw seats 1522*a*, 1522*b*. The central biasing element 1526 can be a coil spring, leaf spring, or any other type of elastic component. As shown in FIG. 18C, the blocking elements 1526*a*, 1526*b* are retained in the base plate 1511 via a mating slot feature. As shown in FIG. 15C, the base plate 1511 defines a slot 1517 with a protrusion 1517' and the blocking element 1526*a* includes a groove 1526*a'*. One of ordinary skill in the art would recognize from the present disclosure that alternative types of retention/mating features can be used to slidingly retain the blocking elements 1526*a*, 1526*b* with the base plate 1511. For example, the retention can be achieved via a t-slot, dovetail, or other mating feature. The blocking elements 1526*a*, 1526*b* are slidingly retained within the slot 1517. In one embodiment, a cover can be integrated into the base plate 1511 that covers the central biasing element 1526 to protect the central biasing element 1526. As shown in FIG. 18C, the blocking elements 1526*a*, 1526*b* define a housing cavity 1527 which is dimensioned to house a portion of the central biasing element 1526. As shown in FIG. 18C, the blocking mechanism 1514 is completely retained within the slot 1517 such that the blocking mechanism 1514 does not extend above an upper surface 1511*a* defined by the base plate 1511. This arrangement provides a lower profile for the plate assembly since the blocking mechanism 1514 does not add any additional height to the plate assembly.

FIGS. 19A-19C and FIG. 20 illustrate another embodiment of a base plate 1911 having a blocking mechanism in accordance with embodiments of the present disclosure. The base plate 1911 is substantially similar to the base plate described above. As such, a description of similar features of the base plate 1911 will be omitted here. The blocking mechanism includes a blocking element 1926 (two blocking elements 1926*a*, 1926*b* shown) disposed in a corresponding groove 2125 (two grooves 2125*a*, 2125*b*) such that a portion of the blocking element protrudes into the bone screw seat 1922 (two bone screw seats 1922*a*, 1922*b* shown). Although only two bone screw seats 1922*a*, 1922*b* are shown here, it should be noted that the base plate 1911 may include four screw seats as discussed above with respect to bone plate 11 or up to twelve screw seats to accommodate more bone screws. The bone screw seat 1922 is substantially similar to the bone screw seats described above. As such, a description of the bone screw seat 1922 is omitted here.

Figure 19A:
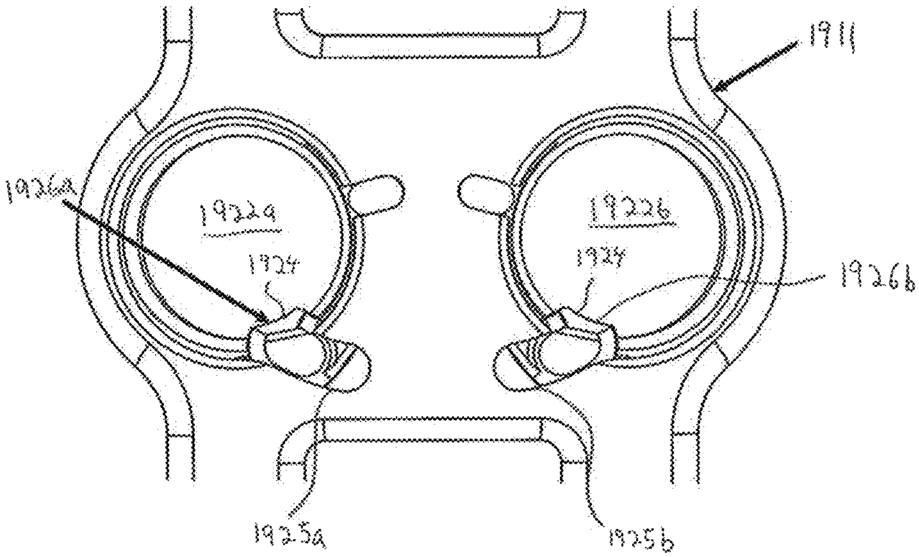
FIG. 19A is a top view of a cervical plate assembly having a blocking mechanism in a blocked position according to one embodiment.
Figure 19B:
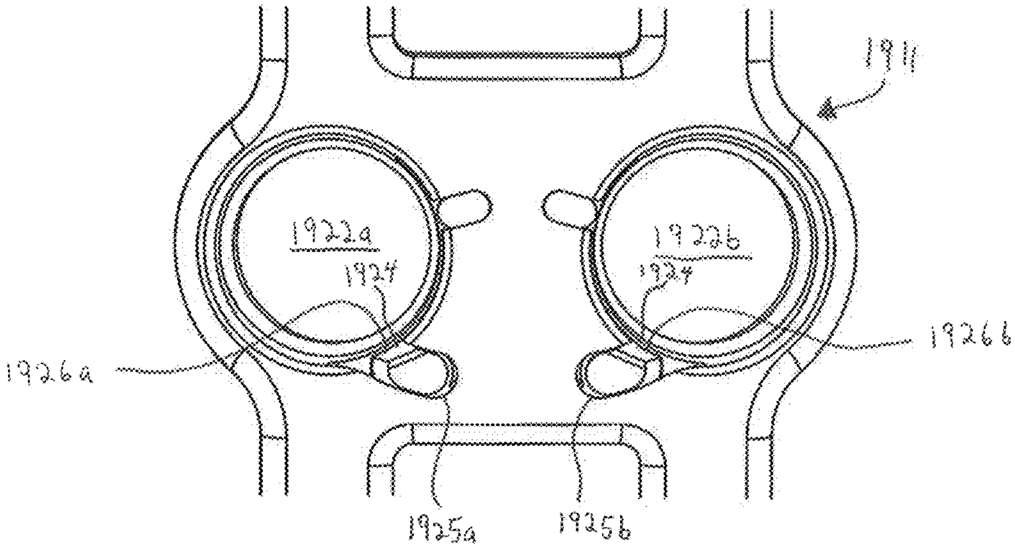
FIG. 19B is a top view of the cervical plate assembly of FIG. 18A in an open position.
Figure 19C:
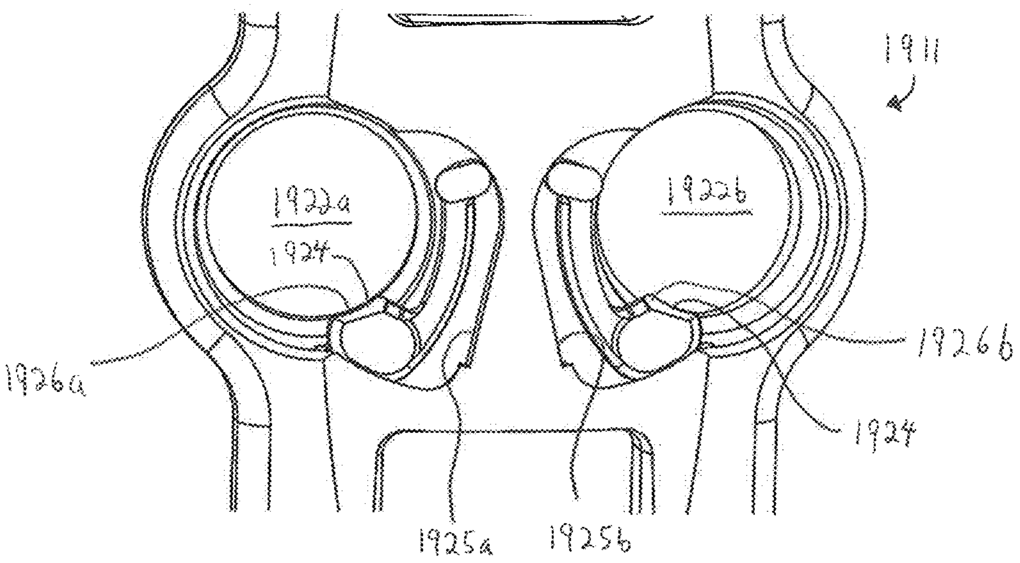
FIG. 19C is a top cross section view of the cervical plate assembly illustrated in FIG. 19B.
Figure 20:
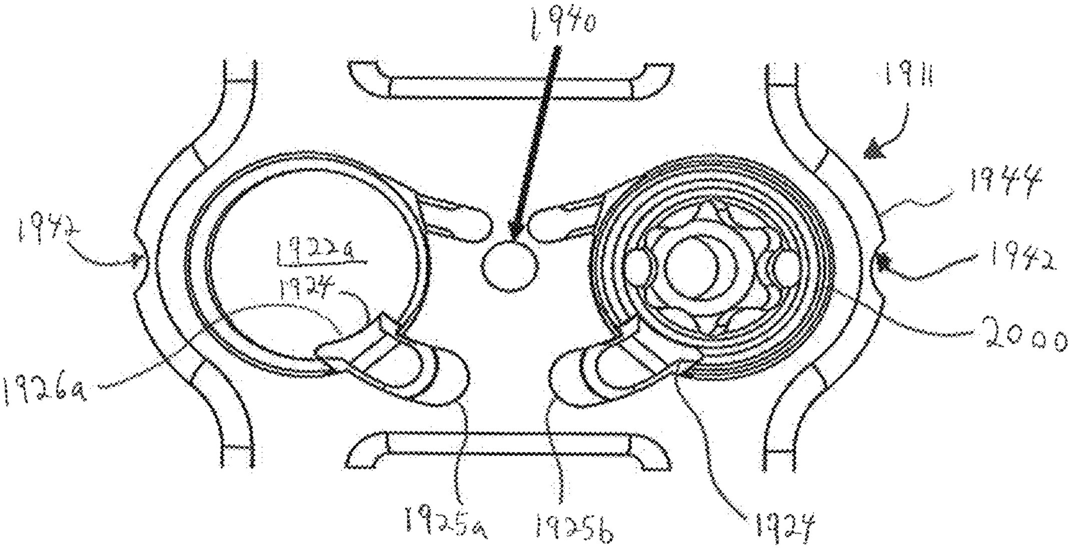
FIG. 20 is a top view of the cervical plate assembly of FIGS. 19A-19C with a fixation element extending therethrough.
Figure 21A:
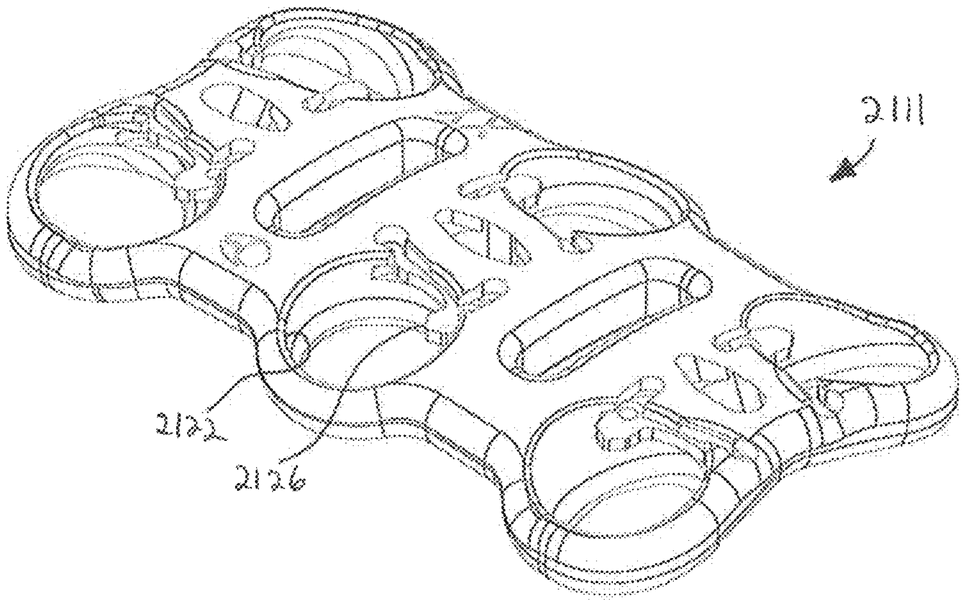
FIG. 21A is a perspective view of a cervical plate assembly according to one embodiment.
Figure 21B:
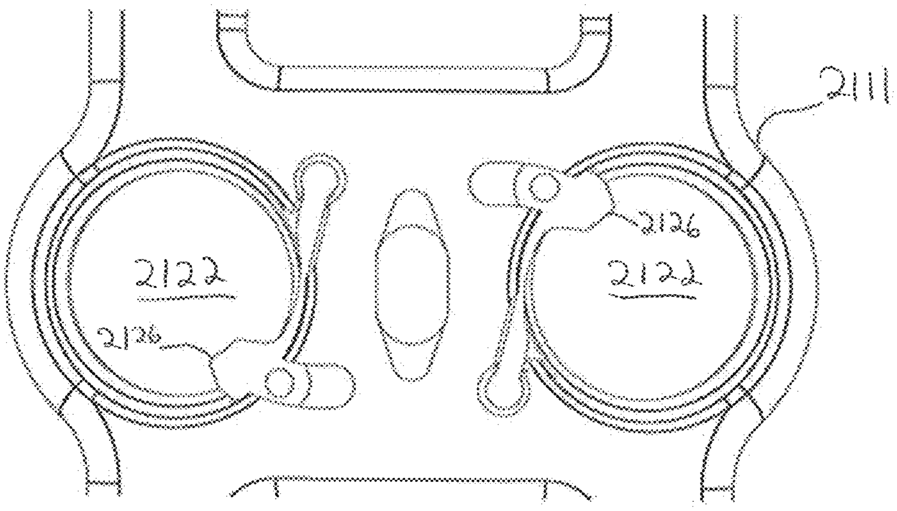
FIG. 21B is a top view of the cervical plate assembly of FIG. 21A having a blocking mechanism in a blocked position.
Figure 21C:
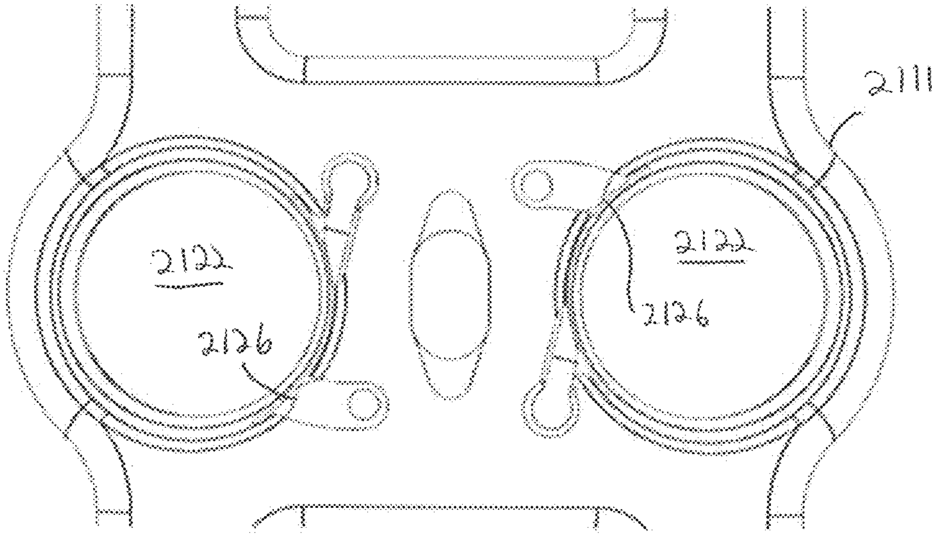
FIG. 21C is a top view of the cervical plate assembly of FIG. 21A having a blocking mechanism in an open position.
Figure 21D:
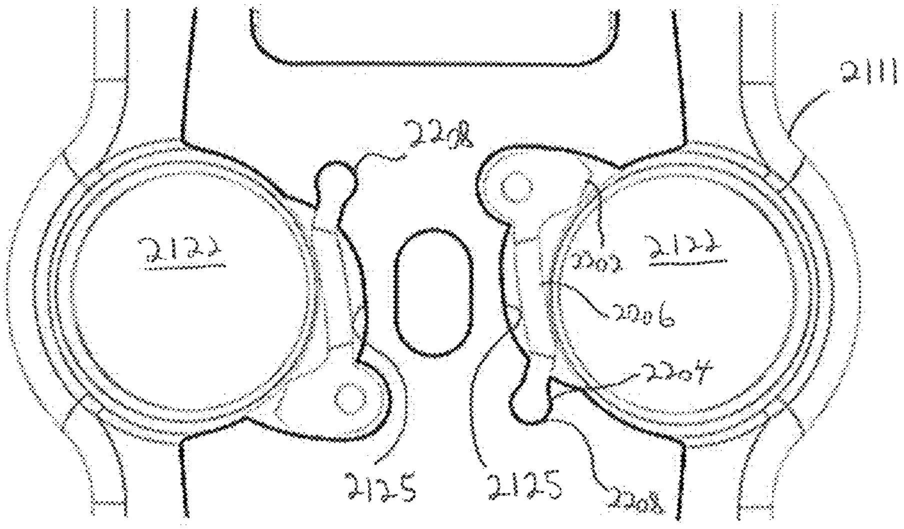
FIG. 21D is a top cross section view of the cervical plate assembly illustrated in FIG. 21C.

In some embodiments, the blocking elements 1926*a*, 1926*b* are bias elements that move between an initial state (shown in FIG. 19A) and a compressed state (shown in FIGS. 19B and 19C). In some embodiments, the blocking elements 1926*a*, 1926*b* are spring elements. As shown in FIG. 19A, the blocking elements 1926*a*, 1926*b* are in the initial state due to their intrinsic biasing force. In this position, the blocking elements 1926*a*, 1926*b* overlap with the bone screw seats 1922*a*, 1922*b* and are in a blocked position to retain the bone screws 2000 within the base plate 1911 (as shown in FIG. 20). In FIG. 19B, the blocking elements 1926*a*, 1926*b* are in a compressed configuration with the blocking elements 1926*a*, 1926*b* being compressed and entirely disposed within corresponding grooves 1925*a*, 1925*b*, which are formed in the base plate 1911 (shown more clearly in the cross-section of FIG. 19C) adjacent to corresponding screw seats 1922*a*, 1922*b*. In this configuration, the blocking elements 1926*a*, 1926*b* are positioned away from the bone screw seats 1922*a* 1922*b* such that the bone screw 2000 can be inserted or removed from the base plate 1911.

During insertion of the bone screw 2000 into one of the screw seats 1922*a*, 1922*b*, the head of the bone screw contacts a ramped surface 1924 of the corresponding blocking element 1926 to deflect the blocking element 1926 away from the screw seat 1922 as the screw 2000 continues to be advanced. After the screw head passes beneath the blocking element 1926, the blocking element 1926 returns to its initial state, thus blocking removal of the screw 2000 from the screw seat 1922 (as shown in FIG. 20). In this locked position, the blocking element 1926 resists screw back out by partially protruding into the screw seat 1922 and contacting a portion of the screw head. The blocking element 1926 advantageously provides tactile feedback to the surgeon so that there is confirmation that the blocking element 1926 has returned to its initial position to block the screw 2000. In addition to this tactile confirmation, the blocking element 1926 also advantageously provides visual confirmation to the surgeon that the blocking element 1926 is being deflected away from the screw seat 1922 during insertion and that the blocking element 1926 has returned to its initial state after the screw 2000 has passes beneath the blocking element 1926. To remove the screw 2000 after it has passed beneath the blocking element 1926, the blocking element 1926 must first be compressed (i.e., moved away from the screw seat 1922). This may be performed using a driver (not shown) having a taper that compresses the blocking element 1926 as the drive tip is inserted into the screw head. Alternatively, there may be a separate instrument that can compress the blocking element 1926 so that a driver can be inserted into the screw head to remove it.

The blocking elements 1926*a*, 1926*b* can be independently moved with respect to each other such that a bone screw 2000 can be inserted or removed from one of the bone screw seats 1922*a*, 1922*b* while a bone screw is blocked in the other one of the bone screw seats 1922*a*, 1922*b*. One of ordinary skill in the art would recognize from the present disclosure that alternative types of blocking elements that elastically deform to retain a screw within the base plate 1911 are within the scope of the present disclosure. For example, the retention can be achieved via a t-slot, dovetail, or other mating feature.

As depicted in FIG. 20, in some embodiments, the base plate 1911 may include a through hole 1940 disposed between two screw seats 1922 and at a midline of the base plate 1911. The through hole 1940 facilitates the insertion of temporary fixation elements (not shown) through the hole 1940 and into a bone (e.g., a vertebra) onto which the plate 1911 is to be coupled to preliminarily capture the plate 1911 onto the bone. In some embodiments, the base plate 1911 may additionally include one or more cuts 1942 formed an outer surface 1944 of the base plate 1911 to allow a tool (not shown) to grasp the base plate 1911 in the predetermined orientation and insert the plate in the predetermined trajectory.

Figure 22:
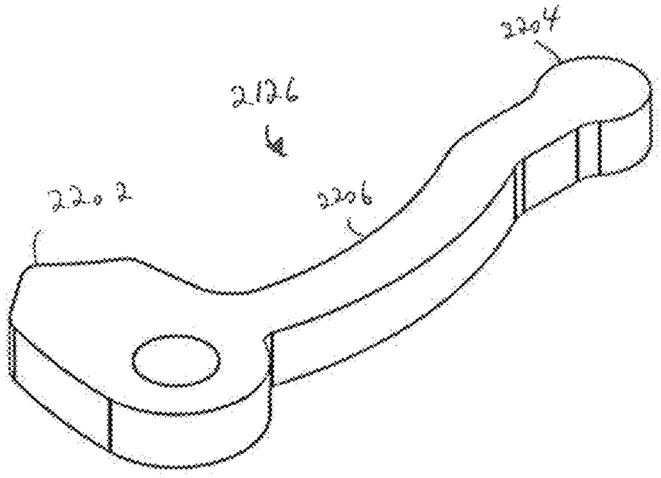
FIG. 22 is a perspective view of a blocking element in accordance with embodiments of the present disclosure.

FIGS. 21A-21D illustrate another embodiment of a base plate 2111 having blocking elements 2126 disposed corresponding screw seats 2122 in accordance with embodiments of the present disclosure. FIG. 22 illustrates a blocking element 2126. The base plate 2111 is substantially similar to the base plate 1911 described above. As such, a description of similar features of the base plate 2111 will be omitted here. Although the base plate 2111 is illustrated as having six screw seats 2122, each having a corresponding blocking element 2126, it should be noted that the base plate 2126 may alternatively have fewer (two or four as with the base plates discussed above) or more (up to twelve) screw seats 2122.

In this embodiment, the blocking element 2126 may alternatively be planar instead of having a ramped surface. As a bone screw (e.g., screw 2000) is inserted into the screw seat 2122, the bottom ramped surface of the screw head contacts an innermost tip 2132 of the blocking element 2126 and moves it towards the compressed state (shown in FIGS. 21C, 21D) as the screw is advanced further through the screw seat 2122. Similar to the blocking element 1926, the blocking element 2126 returns to its initial state (illustrated in FIG. 21A, 21B) after the screw head passes beneath the blocking element 2126 to obstruct the screw seat 2122 and retain the screw within the screw seat 2122.

As depicted in FIG. 22, the blocking element 2126 is a monolithic planar element having a blocking portion 2202, a base portion 2204, and an arm 2206 coupling the blocking portion 2202 to the base portion 2204. In some embodiments, the base portion 2204 has a bulbous shape and is retained in a correspondingly shaped opening 2208 formed in the base plate 2111 (shown more clearly in the cross-section of FIG. 21D). When the blocking element 2126 is compressed by the screw head, the blocking portion 2202 is pushed into a groove 2125 formed in the base plate 2111 such that the screw seat 2122 is unobstructed.

Figure 23:
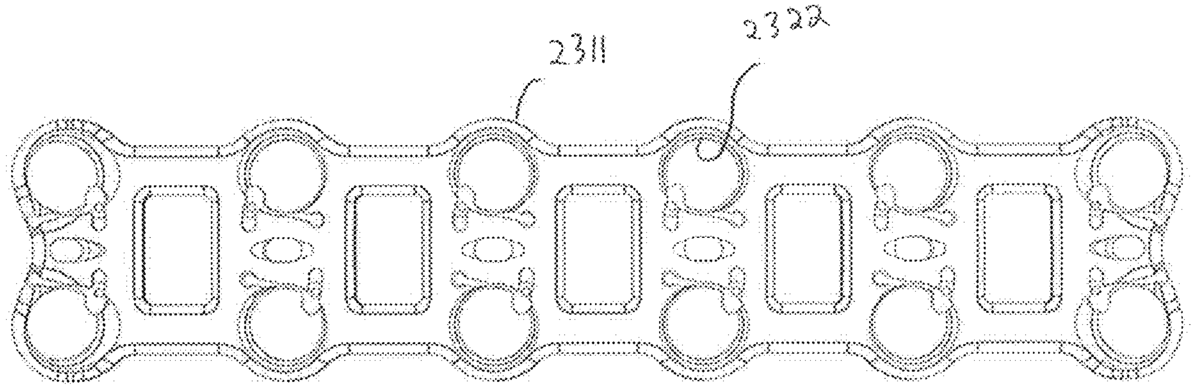
FIG. 23 is a top view of a cervical plate assembly according to one embodiment.

Although several embodiments have been disclosed in the foregoing specification, it is understood that many modifications and other embodiments will come to mind, having the benefit of the teaching presented in the foregoing description and associated drawings. It is thus understood that the scope of the embodiments described herein are not limited to the specific embodiments disclosed hereinabove, and that many modifications and other embodiments are intended to be included within the scope of the appended claims. For example, although the base plates (e.g. base plates 11, 1911, 1511, 2111) are shown with two or four screw seats, it should be noted that the present disclosure encompasses a base plate 2311 having up to twelve screw seats 2322, as depicted in FIG. 23.

The above-disclosed base plates may utilize a variety of different fixation elements to secure the base plate to a vertebra such as, for example, fixed angle screws, variable angle screws, self-drilling tip screws, self-tapping tip screws, primary diameter screws, rescue diameter screws, and double rescue diameter screws. FIGS. 24A-24B, 25A-25B, 27, and 28 depict examples of fixation elements (e.g., screws) for use with the base plates (e.g. base plates 11, 1911, 1511, 2111) in accordance with embodiments of the present disclosure. FIGS. 26A-26B depict a cervical plate assembly with the screws of FIGS. 24A-25B in accordance with embodiments of the present disclosure.

When comparing fixed angle screws with variable angle screws, there is a difference in a diameter of the necks of the screws. Each screw consists of a spherical screw head with a drive feature used to thread the screw into the bone. This spherical screw head sits in a corresponding spherical hole in the base plate, which provides the capability of polyaxial motion of the screw. The fixed angle screw has a larger neck diameter which allows for less angulation in the plate compared to the variable angle screw. Such a scenario may be beneficial when, for example, a surgeon wants to limit post-operative settling. The variable angle screw has a smaller neck diameter which allows for more angulation of the screw in the plate. Additionally, different types of fixation elements may include identifying features to clearly distinguish them from one another. For example, as will be discussed below, screw heads may include a predetermined pattern of cuts and laser marks to distinguish the various types of fixation elements (i.e., screws) from one another.

Figure 24A:
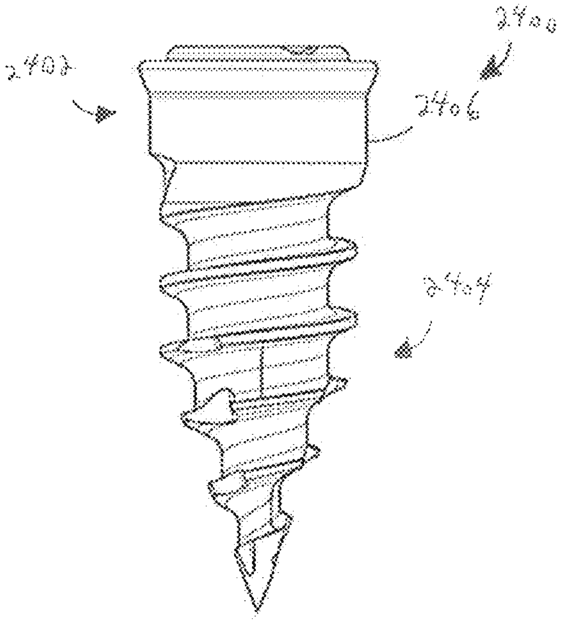
FIGS. 24A-24B depict an example of a fixation element for use with a cervical plate assembly in accordance with embodiments of the present disclosure.
Figure 24B:
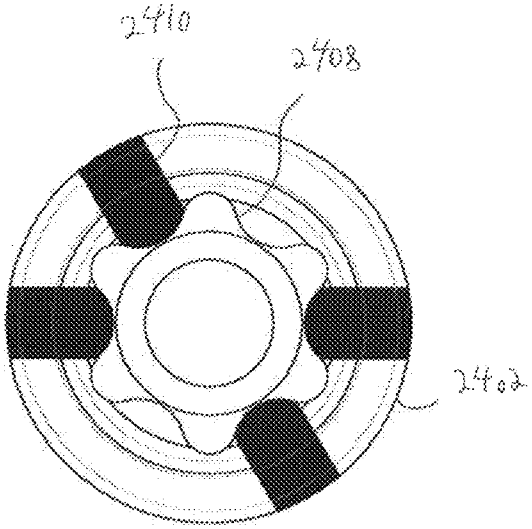

FIGS. 24A-24B depict a fixed angle screw 2400. As illustrated in FIG. 24A, the screw 2400 includes a head 2402, a threaded shaft 2404 extending from the head 2402, and a neck portion 2406 disposed between the head 2402 and the threaded shaft 2404. As illustrated in FIG. 24B, the screw head 2402 includes a tool engagement feature 2402 so that driver (not shown) can engage the screw 2400 and drive it into a bone. The screw head 2402 further includes identifying features 2410. In some embodiments, the identifying features 2410 may be cutouts filled with laser marks and arranged in a predetermined configuration to identify the screw 2400 as a fixed angle screw.

Figure 25A:
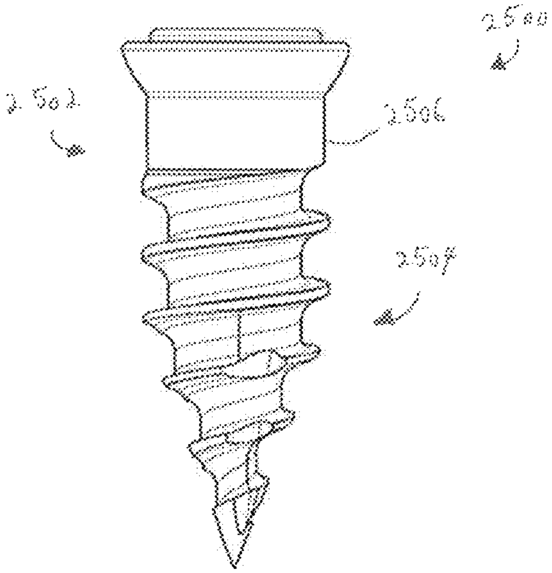
FIGS. 25A-25B depict an example of a fixation element for use with a cervical plate assembly in accordance with embodiments of the present disclosure.
Figure 25B:
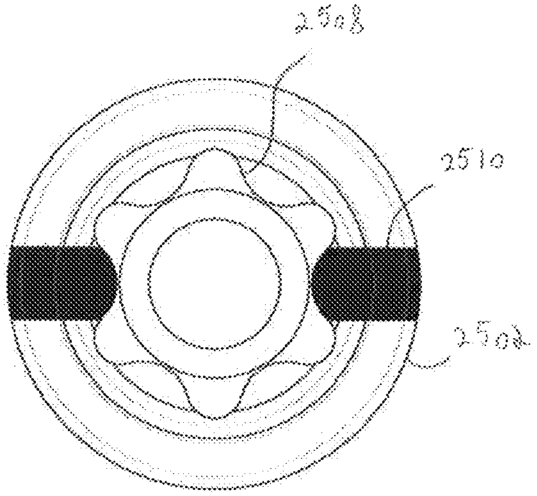
Figure 26A:
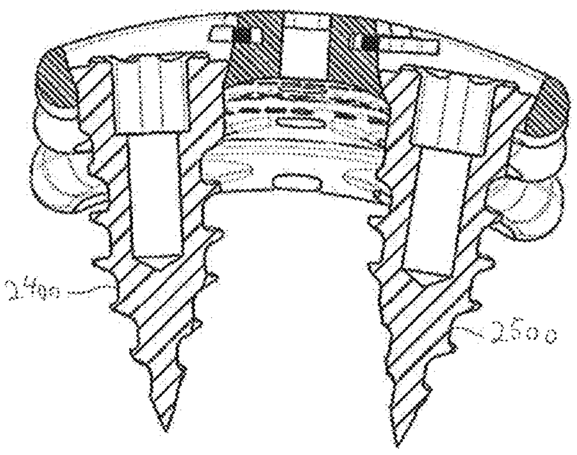
FIGS. 26A-26B depict a cervical plate assembly with the screws of FIGS. 24A-25B in accordance with embodiments of the present disclosure.
Figure 26B:
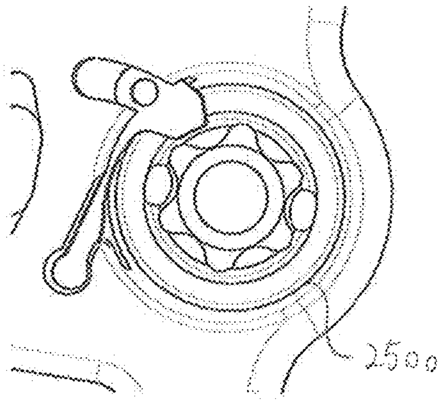

FIGS. 25A-25B depict a variable angle screw 2500. As illustrated in FIG. 25A, the screw 2500 includes a head 2502, a threaded shaft 2504 extending from the head 2502, and a neck portion 2506 disposed between the head 2502 and the threaded shaft 2504. As illustrated in FIG. 25B, the screw head 2502 includes a tool engagement feature 2502 so that driver (not shown) can engage the screw 2500 and drive it into a bone. The screw head 2502 further includes identifying features 2510. In some embodiments, the identifying features 2510 may be cutouts filled with laser marks and arranged in a predetermined configuration to identify the screw 2500 as a variable angle screw.

As noted above, the base plates of the present disclosure may include various different fixation elements. For example, as depicted in FIG. 26A, the base plate may include the fixed angle screw 2400 disposed in one screw seat and the variable angle screw 2500 disposed in a different screw seat. FIG. 26B is a top view of the variable angle screw 2500 disposed in its screw seat with the blocking element disposed above the screw head to prevent any possible backing out of the screw.

Figure 27:
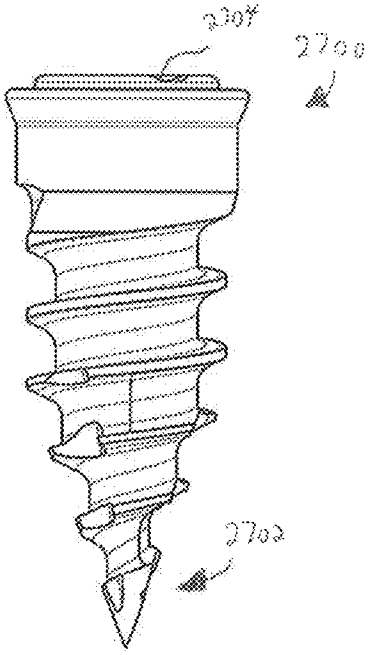
FIG. 27 depicts an example of a fixation element for use with a cervical plate assembly in accordance with embodiments of the present disclosure.
Figure 28:
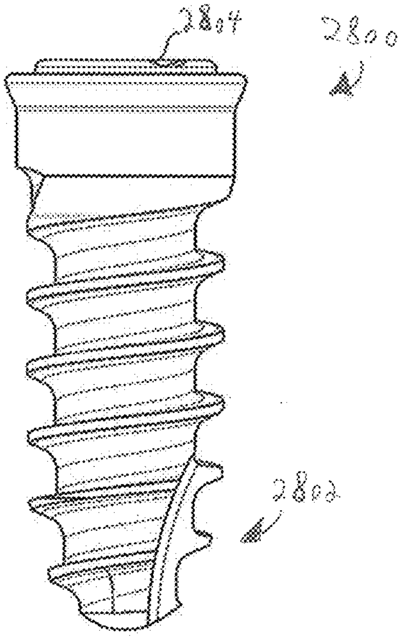
FIG. 28 depicts an example of a fixation element for use with a cervical plate assembly in accordance with embodiments of the present disclosure.

FIGS. 27 and 28 depict additional examples of different fixation elements that may be used with the base plates of the present disclosure. FIG. 27 depicts a screw 2700 having a self-drilling tip 2702. FIG. 28 depicts a screw having a self-tapping tip 2802. The self-drilling tip 2702 is sharp, which allows a user to insert the screw 2700 without drilling a pilot hole in the bone. The self-tapping tip 2802 is blunt, which requires a user to pre-drill pilot hole prior to inserting the screw 2800. In some embodiments, the screws may also include a cut 2704, 2804 on the top of the screw head to allow for additional clearance blocking element. This advantageously helps block the screw disposed in the screw seat by keeping the screw head contact surface farther away from the blocking element.

It is further envisioned that features from one embodiment may be combined or used with the features from a different embodiment described herein. Moreover, although specific terms are employed herein, as well as in the claims which follow, they are used only in a generic and descriptive sense, and not for the purposes of limiting the described embodiments, nor the claims which follow.

What is claimed is:

1. A plate assembly having locking features, the assembly comprising:
- a base plate including:
- a bone screw seat including a borehole dimensioned to receive a bone screw, and
- a blocking seat positioned near the bone screw seat; and
- a blocking mechanism retained within the blocking seat and having an elastically deformable portion that, in a locked position, has a resilient portion which deforms upon contact with a bone screw placed into the borehole and extends over the bone screw seat after the screw is placed in the borehole, wherein the elastically deformable portion is manually movable to an unlocked position without being deformed prior to removal of the inserted bone screw,
- wherein the elastically deformable portion of the blocking mechanism is in the form of a lobe, and the blocking mechanism has opposing cutouts and lobes disposed between the opposing cutouts, and wherein each lobe has a slot configured to engage a driver tool.

2. The plate assembly of claim 1, wherein the elastically deformable portion of the blocking mechanism is configured to be manually slid away from the bone screw seat to place the blocking mechanism in the unlocked state.

3. The plate assembly of claim 1, wherein the elastically deformable portion of the blocking mechanism is configured to be manually rotated to move the elastically deformable portion away from the bone screw seat to place the blocking mechanism in the unlocked state.

4. The plate assembly of claim 1, wherein the blocking mechanism includes:
- a head having an engagement recess for engaging the driver tool; and
- each lobe extends laterally from the recess and configured to deflect inwardly when the bone screw is inserted.

5. The plate assembly of claim 4, wherein the head includes a concave circumferential edge that forms each cutout and a convex circumferential edge that forms each lobe.

6. A vertebral plate assembly having locking features, the assembly comprising:
- a base plate adapted to fix one vertebral body to an adjacent vertebral body and including:
  - a bone screw seat including a borehole dimensioned to receive a bone screw, and
  - a blocking seat positioned near the bone screw seat; and
  - a blocking mechanism retained within the blocking seat and having a resilient portion disposed over the bone screw seat, the blocking mechanism having a locked state and an unlocked state, wherein:
    - in the locked position, the resilient portion, deforms upon contact with a bone screw placed into the borehole and extends over the bone screw seat after the screw is placed in the borehole; and
    - the elastically deformable portion is manually movable to the unlocked position to position the resilient portion away from the bone screw seat without being deformed prior to removal of the inserted bone screw,
  - wherein the elastically deformable portion of the blocking mechanism is in the form of a lobe, and the blocking mechanism has opposing cutouts and lobes disposed between the opposing cutouts, and wherein each lobe has a slot configured to engage a driver tool.

7. The vertebral plate assembly of claim 6, wherein the resilient portion of the blocking mechanism is configured to be manually slid away from the bone screw seat to place the blocking mechanism in the unlocked state.

8. The vertebral plate assembly of claim 6, wherein the resilient portion of the blocking mechanism is configured to be manually rotated to move the resilient portion away from the bone screw seat to place the blocking mechanism in the unlocked state.

9. The vertebral plate assembly of claim 6, wherein the blocking mechanism includes:
- a head having an engagement recess for engaging the driver tool; and
- each lobe extends laterally from the recess and configured to deflect inwardly when the bone screw is inserted.

10. The vertebral plate assembly of claim 9, wherein the head includes a concave circumferential edge that forms each cutout and a convex circumferential edge that forms each lobe.

* * * * *